United States Patent
Gertsenshteyn et al.

(10) Patent No.: US 7,231,017 B2
(45) Date of Patent: Jun. 12, 2007

(54) LOBSTER EYE X-RAY IMAGING SYSTEM AND METHOD OF FABRICATION THEREOF

(75) Inventors: Michael Gertsenshteyn, Torrance, CA (US); Thomas Forrester, Westminster, CA (US); Tomasz Jannson, Torrance, CA (US); Kang Lee, Woodland Hills, CA (US); Gajendra Savant, Rolling Hills Estates, CA (US)

(73) Assignee: Physical Optics Corporation, Torrance, CA (US)

( * ) Notice: Subject to any disclaimer, the term of this patent is extended or adjusted under 35 U.S.C. 154(b) by 99 days.

(21) Appl. No.: 11/191,095

(22) Filed: Jul. 27, 2005

(65) Prior Publication Data

US 2007/0025512 A1  Feb. 1, 2007

(51) Int. Cl.
*G01N 23/203* (2006.01)
*G21K 1/06* (2006.01)

(52) U.S. Cl. .......................... 378/87; 378/84; 378/86; 378/149; 250/505.1

(58) Field of Classification Search ............ 378/44–50, 378/84, 85, 86–90, 147, 149, 154, 155; 250/505.1
See application file for complete search history.

(56) References Cited

U.S. PATENT DOCUMENTS

| | | | | |
|---|---|---|---|---|
| 2,741,710 A | * | 4/1956 | Bartow et al. | 378/149 |
| 4,196,351 A | * | 4/1980 | Albert | 378/98.6 |
| 5,029,337 A | * | 7/1991 | MacKenzie et al. | 378/90 |
| 5,099,134 A | * | 3/1992 | Hase et al. | 250/505.1 |
| 5,222,113 A | * | 6/1993 | Thieme et al. | 378/43 |
| 5,270,549 A | * | 12/1993 | Engdahl | 250/505.1 |
| 5,479,469 A | * | 12/1995 | Fraser et al. | 378/149 |
| 5,619,382 A | * | 4/1997 | Kato et al. | 359/858 |
| 5,727,044 A | * | 3/1998 | Fraser et al. | 378/149 |
| 5,933,473 A | * | 8/1999 | Kitaguchi et al. | 378/57 |
| 5,978,445 A | * | 11/1999 | Schultheiss et al. | 378/82 |
| 6,452,184 B1 | * | 9/2002 | Taskar et al. | 250/367 |
| 6,754,304 B1 | * | 6/2004 | Kumakhov | 378/45 |
| 6,782,076 B2 | * | 8/2004 | Bowen et al. | 378/74 |
| 6,881,965 B2 | * | 4/2005 | Bowen et al. | 250/492.2 |
| 7,078,700 B2 | * | 7/2006 | Chandhok et al. | 250/363.1 |
| 7,149,279 B2 | * | 12/2006 | Kumakhov et al. | 378/71 |
| 2006/0261290 A1 | * | 11/2006 | Van Herpen et al. | 250/492.2 |

* cited by examiner

*Primary Examiner*—Allen C. Ho
(74) *Attorney, Agent, or Firm*—Leonard Tachner

(57) ABSTRACT

A Lobster Eye X-ray Imaging System based on a unique Lobster Eye (LE) structure, X-ray generator, scintillator-based detector and cooled CCD (or Intensified CCD) for real-time, safe, staring Compton backscatter X-ray detection of objects hidden under ground, in containers, behind walls, bulkheads etc. In contrast to existing scanning pencil beam systems, Lobster Eye X-Ray Imaging System's true focusing X-ray optics simultaneously acquire ballistic Compton backscattering photons (CBPs) from an entire scene irradiated by a wide-open cone beam from one or more X-ray generators. The Lobster Eye X-ray Imaging System collects (focuses) thousands of times more backscattered hard X-rays in the range from 40 to 120 keV (or wavelength $\lambda=0.31$ to 0.1 Å) than current backscatter imaging sensors (BISs), giving high sensitivity and signal-to-noise ratio (SNR) and penetration through ground, metal walls etc. The collection efficiency of Lobster Eye X-ray Imaging System is optimized to reduce emitted X-ray power and miniaturize the device. This device is especially advantageous for and satisfies requirements of X-ray-based inspection systems, namely, penetration of the X-rays through ground, metal and other material concealments; safety; and man-portability. The advanced technology disclosed herein is also applicable to medical diagnostics and military applications such as mine detection, security screening and a like.

21 Claims, 14 Drawing Sheets

$$\frac{1}{x} - \frac{1}{y} = -\frac{2}{R} = -\frac{1}{f}; \quad f = \frac{R}{2}$$

$2\alpha$ — GEOMETRICAL APERTURE $\beta = \gamma + \theta_c, \theta_c = \alpha + \gamma, \beta = 2\gamma + \alpha$ $\theta_c$ — CRITICAL ANGLE (GRAZING)

$\Delta R$ — DEPARTURE FROM THIN LENS APPROXIMATION t = thickness of rib
u = slot depth
2u = overall rib height
s, s' = width of slot

LOBSTER EYE X-RAY IMAGING SYSTEM AND METHOD OF FABRICATION THEREOF

BACKGROUND OF THE INVENTION

1. Field of the Invention

The present invention relates to an improved X-ray imaging system employing lobster eye X-ray focusing technology.

2. Background Art

Many industrial and military applications require the capability for non-invasive inspection of objects through the concealments, walls, ground, bulkheads of boat and ship containers. For this purpose, agencies are seeking a portable (or handheld) instrument that can accurately analyze and visualize material hidden from view behind ground, walls, and bulkheads. The inspection device must not endanger inspection personnel, must be simple to operate, must minimize disruption of commercial and private property, while ensuring full space accountability. The immediate application is detection by inspection personnel of illegal cargo, and other contraband in ocean-going containers, aboard ships and boats, in airports and other check-points and also landmines and improvised explosive devices (IEDs).

Means of through-wall or through-ground inspection include optical, microwave, acoustic and X-ray techniques. The optical thermal imaging systems cannot see hidden objects that are at the same temperature as the walls. Acoustic systems do not penetrate well through metal walls, and their low frequencies are dangerous to operators and stowaways. Microwave radars cannot penetrate metal bulkheads. Although state-of-the-art X-ray scanning BISs can penetrate walls and internal construction structures, they are bulky, expensive, and above all hazardous. To assemble an X-ray image, the current BISs use expensive, massive, limited view, scintillation detectors with photomultiplier tubes (PMTs) and a scanning pencil beam of X-rays. Generating the scanning pencil beam is both inefficient and hazardous to the operator, and a person hiding behind a wall. This is not a safe handheld, man-portable instrument. Therefore, state-of-the-art X-ray inspection systems also fail to meet requirements for ship compartment inspection.

SUMMARY OF THE INVENTION

To overcome these limitations, the present invention incorporates a new, Lobster Eye X-ray Imaging System based on a unique Lobster Eye (LE) structure, X-ray generator, scintillator crystal, CCD (or Intensified CCD) and image processing module for real-time, safe, starting Compton backscatter X-ray detection of objects hidden under ground, in containers, behind walls, bulkheads etc. In contrast to existing scanning pencil beam systems, Lobster Eye X-ray Imaging System's true focusing X-ray optics simultaneously acquire ballistic Compton backscattering photons (CBPs) from an entire scene irradiated by a wide-open cone beam from an X-ray generator (staring). The Lobster Eye X-ray Imaging System collects (focuses) thousands of times more backscattered hard X-rays in the range from 40 to 120 keV (or wavelength $\lambda$=0.31 to 0.1 Å) than current BIS devices, giving high sensitivity and signal-to-noise ratio (SNR) and penetration through metal walls. The collection efficiency of Lobster Eye X-ray Imaging System is optimized to reduce emitted X-ray power and miniaturize the device. This device satisfies requirements of X-ray-based inspection: penetration of the X-rays through ground, metal and other bulkheads; safety of inspection personnel; and man-portability. An important advantage of Lobster Eye X-ray Imaging System is that it can penetrate ground, walls, bulkheads, and hulls, including metal ones, while protecting human safety when the following considerations are met.

The design of Lobster Eye X-ray Imaging System is based on the following considerations:

The energy range optimal for backscattering is from 40 to 120 keV, the same as for routine medical X-ray chest examination; 42% of 50 keV (or $\lambda$=0.25 Å) X-ray photons penetrate a 30 mil steel wall (equivalent to 1 in. of plastic, or 8 in. of dry wood);

The total dose of X-ray irradiation of inspection personnel is crucial. This dose is a function both of the number of photons and of their energy. By preliminary estimates, the operator of a Lobster Eye X-ray Imaging System for inspection of cargo and the like will receive radiation comparable with natural radiation level.

Lobster Eye X-ray Imaging System operation for inspection of cargo involves following real-time processes:

Irradiating an object behind concealment with open cone of X-rays;

Collecting the backscattering ballistic X-ray photons;

Processing information accumulated within multiple CCD frames;

Retrieving the faint X-ray images of hidden objects with high angular resolution.

The advantages of the disclosed Lobster Eye X-ray Imaging System technology over current approaches include:

Observes Compton backscattering through metallic and other walls with safe levels of irradiation for operator;

Acquires X-ray images instantaneously over the entire FOV by staring, that is, without scanning;

Makes use of all X-ray flux from, X-ray generator, in contrast to existing bulky pencil-beam scanning systems;

Has high angular resolution for remote detection of X-ray CBPs;

Significantly enhances X-ray intensity in the focal spot compared to the diffuse background, and therefore has SNR and sensitivity that are significantly better than those of other X-ray sensors, despite much lower safe X-rays intensity levels;

Is preferably handheld, man-portable, and easy to fabricate with cost-effective, components and technologies.

The Lobster Eye X-ray Imaging System exactly meets the need for real-time (no latency) detection of IEDs or through-wall imaging of contraband in containers, trucks, ships and boats by means of Compton backscattered photons. It penetrates metallic walls, is safe for inspector personnel, and has enhanced resolution and SNR because of the true focusing capability of the lobster eye (LE) X-ray optics.

The most significant feature of the disclosed embodiment is a highly innovative fabrication and assembly concept for the lobster eye lens structure. This concept permits all polishing and finishing to be carried out on flat parts and achieves a perfectly formed LE configuration with true 90 degree corners and high geometric precision.

Other aspects of the invention herein relate to the optical characteristics of the lobster eye lens including the compensation of defocusing resulting from the proximate location of the backscatter targets and the energy distribution of the incident X-rays. Use of the lobster eye lens as a spectrometer, which may be useful in analyzing wall materials, is also disclosed.

The novel imaging system disclosed herein also finds advantageous application in medical diagnosis and military uses such as mine detection and the like.

The following references are noted herein by corresponding numbers:
1. J. W. Goodman, "Introduction to Fourier Optics", ($2^{nd}$ Edition), McGraw-Hill, 1996
2. U.S. Pat. No. 5,497,008
3. U.S. Pat. No. 5,192,869
4. P. Gorenshtein, E. Whitbeck, G. Austin, and A. Kentev, "Lobster-Eye X-Ray Telescope Prototype," SPIE, vol. 2805, pp. 74–81, 1996.
5. S. S. Holt, "All-Sky Monitors for X-Ray Astronomy," Space Science Reviews, vol. 45, pp. 269–289, 1987.
6. W. C. Priedhorsky, A. G. Peele, and K. A. Nugent, "An X-Ray All-Sky Monitor with Extraordinary Sensitivity," Mon. Not. R. Astron. Soc., vol. 279, pp. 733–750, 1996.
7. G. K. Parks, S. H. Werden, and M. P. McCarthy, "Pinhole X-Ray Cameras for Imaging Small-Scaled Auroral Structures," Opt. Eng., vol. 32, no. 12, pp. 3164–3168, 1993.
8. J. R. P. Angel, "Lobster-Eyes as X-Ray Telescopes," Ap. J., vol. 233, pp. 364–373, 1979.
9. M. F. Land and D. Nilsson, "Animal Eyes," Oxford University Press, 2002
10. J. Macdonald et al., "Alternatives for Landmine Detection," RAND Organization, pp. 191–223, 2003 www.rand.org.
11. E. T. Dugan, and A. M. Jacobs, Lateral Migration Radiology Image Signature for the Detection and Identification of Buried Land Mines, Final Progress Report to the US Army Research Office, ARO Grant DAAG-55-98-1-0400, August 2001.
12. W. J. Baukus, "X-Ray Imaging for On-The-Body Contraband Detection," Presented to 16th Annual Security Technology Symposium & Exhibition, Jun. 28, 2000.
13. W. Niemann, et al, "Detection of Buried Landmines with X-Ray Backscatter Technology," The e-Journal of Nondestructive Testing, vol. 7, no. 10, www.ndt.net/index.html, October 2002.
14. G. J. Lockwood, et al. "Bomb Detection Using Backscattered X-Rays," SPIE Proceedings, vol. 3577, pp. 53–61, 1999.
15. G. W. Fraser, and A. N. Brunton, et al., "Lobster-ISS: An Imaging X-ray All-sky Monitor for the International Space Station," Proc. SPIE, X-Ray and Gamma-Ray Instrumentation for Astronomy XII, Kathryn A. Flanagan, Oswald H. Siegmund, vol. 4497, pp. 115–126, January 2002.

BRIEF DESCRIPTION OF THE DRAWINGS

The various embodiments, features and advances of the present invention will be understood more completely hereinafter as a result of a detailed description thereof in which reference will be made to the following drawings.

DETAILED DESCRIPTION OF PREFERRED EMBODIMENTS

Lobster Eye Imaging for Non-Astronomical Objects

Figure 1:
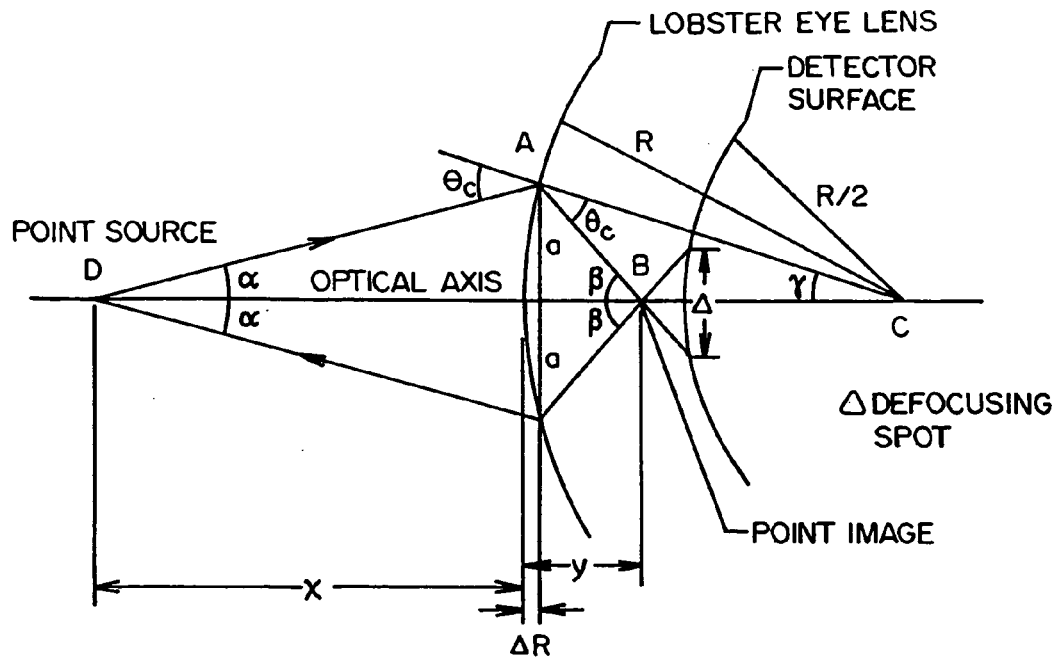
FIG. 1 is a schematic representation of lobster eye lens operation geometry for finite distance object.

Prior applications of the lobster eye lens have focused on astronomical objects; i.e., objects in infinity (x=∞). Then, spherical aberration dominates. In contrast, in the case of non-astronomical objects; i.e., objects in finite distances, comparable with lobster eye lens radius, R (x~R), defocusing dominates, since the image region changes its location. To show this, consider the lobster eye lens geometry in FIG. 1. To derive lobster eye imaging equation, consider point source, D, its image, B, and curvature center, C. The local optical axis, DC, connects D with C. For continuum of objects points, we have a continuum of such axes, in contrast to the typical optical lens system that has only one axis. From triangle ABC, we have:

$$\beta = 2\gamma + \alpha \qquad (1)$$

and, from triangle DAC, we have $$\theta_c = \alpha + \gamma \qquad (2)$$

where $\theta_c$—cutoff angle of total external reflection (TER), that is, typically, in the range of 0.3°–0.5°. For such small TER-angles, Equation (1) can be transformed to the following lens imaging equation:

$$\frac{a}{y} = \frac{2a}{R} + \frac{a}{x}, \text{ or } \frac{1}{y} = \frac{2}{R} + \frac{1}{x}, \text{ or} \quad (3)$$

$$\frac{1}{x} - \frac{1}{y} = -\frac{2}{R}; \text{ or, } \frac{1}{y} = \frac{1}{f} + \frac{1}{x} \quad (4)$$

$$\text{where } f = \frac{R}{2} \quad (5)$$

This is the image equation for the lobster eye lens at finite object distances, x. From Equations (4) and (5), the defocusing, $\Delta y$, is $$\Delta y = f - y = \frac{y}{x}f = \frac{f^2}{x+f} = f\frac{1}{1+\frac{x}{f}} \quad (6)$$

which can be significant, for small (x/f)-ratios. For example, for R=6 cm, f=3 cm, and x=1 m, we have $\Delta y$=0.9 mm; while for x=50 cm, and 20 cm, we have $\Delta f$=1.7 mm and 3.9 mm, respectively. The relative change of defocusing is comparable (smaller) with a relative change of object distance:

$$\left|\frac{d(\Delta y)}{\Delta y}\right| = \left(\frac{x}{x+f}\right)\left|\frac{dx}{x}\right| = \left(\frac{1}{1+\frac{f}{x}}\right)\left|\frac{dx}{x}\right| \leq \left|\frac{dx}{x}\right| \quad (7)$$

For example, when distance, x, changes by 1%, the defocusing changes by less than 1%. The defocusing spot, $\Delta$, has the form:

$$\frac{\Delta}{R\theta_c} = \frac{1}{1+\frac{x}{R}} \quad (8)$$

that is summarized in Table 1.

TABLE 1

Defocusing Spots $\Delta$ for R = 6 cm

| x | $\frac{x}{R}$ | $\frac{\Delta}{R\theta_c}$ | $\frac{\Delta}{\theta_c = 0.01}$ | $\frac{\Delta}{\theta_c = 0.3°}$ |
|---|---|---|---|---|
| 1 m | 16.7 | 0.06 | 36 μm | 18 μm |
| 50 cm | 8.3 | 0.10 | 60 μm | 30 μm |
| 20 cm | 3.3 | 0.23 | 138 μm | 69 μm |

The lobster eye lens imaging Equations (3) or (4), have been derived under paraxial conditions, which is automatically satisfied due to: $\theta_c \ll 1$. The second assumption was that lobster eye channels have a width-to-length ratio $\sim \theta_c$ in radians, so only one (or two in 3D) TER is considered, as in FIG. 1, where only a single optical axis is shown. In fact, such an axis can be provided for any point source around the lobster eye lens. So the set of optical axes is a continuum, or discrete set, if discretization of the detector surface (in the form of pixels) is provided.

The lobster eye geometrical aperture has an area of $\pi a^2$, where a—is its radius, in the form:

$$\frac{a}{R\theta_c} = \frac{1}{1+\frac{R}{x}} \quad (9)$$

Summarized in Table 2.

TABLE 2

Geometrical Aperture Diameters, 2a, for R = 6 cm

| x | $\frac{R}{x}$ | $\frac{\Delta}{\theta_c R}$ | $\frac{2a}{\theta_c = 0.01}$ | $\frac{2a}{\theta_c = 0.3°}$ |
|---|---|---|---|---|
| 1 m | 0.06 | 0.94 | 1.1 mm | 0.55 mm |
| 50 cm | 0.12 | 0.89 | 1.0 mm | 0.50 mm |
| 20 cm | 0.30 | 0.77 | 0.9 mm | 0.45 mm |

Since the performance of the lobster eye lens is better for higher a-values (better collection power), and lower $\Delta$-values (lower defocusing, which provides a blurred image), we can introduce the lens quality coefficient, Q, in the form:

$$Q \triangleq \frac{a}{\Delta} \quad (10)$$

From Equations (8) and (9), we have $$Q = \frac{x}{R} \quad (11)$$

i.e., proportional to x-distance. Higher distance, better lens performance.

Figure 2:
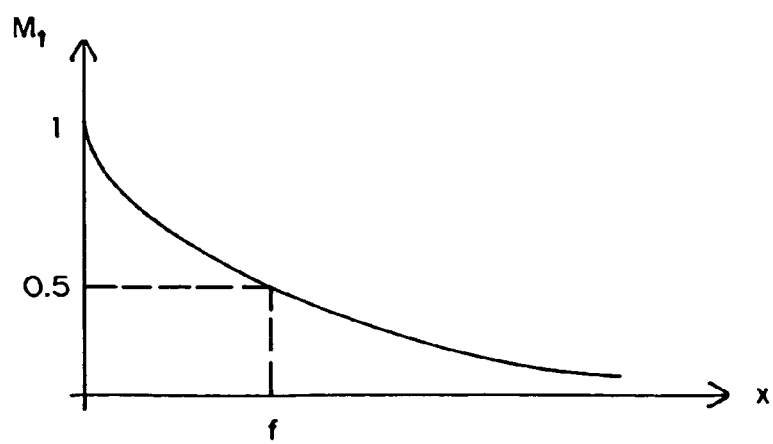
FIG. 2 is a graph illustrating dependence of the transversal magnification $M_t$ of LE lens as function of the distance to an object analogically to a convex mirror.

There are three usual lens magnifications: transversal; ($M_t$) angular ($M_\theta$), and longitudinal ($M_l$) where $$M_t = \frac{1}{1+\frac{x}{f}} \quad (12a)$$

$$M_\theta = 1 + \frac{x}{f} \quad (12b)$$

$$M_l = (M_t)^2 \quad (12c)$$

where $M_t$-value is illustrated in FIG. 2.

FIG. 2 shows an analogy between lobster eye lens and a convex mirror. We see that the imaging equation (4) also holds for a convex mirror, except we need to replace the real image in the lobster eye case with a virtual image in the mirror case. Thus, image aberrations remain the same in both cases, except in the case of the lobster eye, the paraxial approximation is automatically satisfied (due to $\theta_c \ll 1$); thus, third order (Seidel) geometrical aberrations are very small in the case of the lobster eye lens, reduced to spherical aberration in the astronomical case (where x=∞).

Apodization

Figure 3:
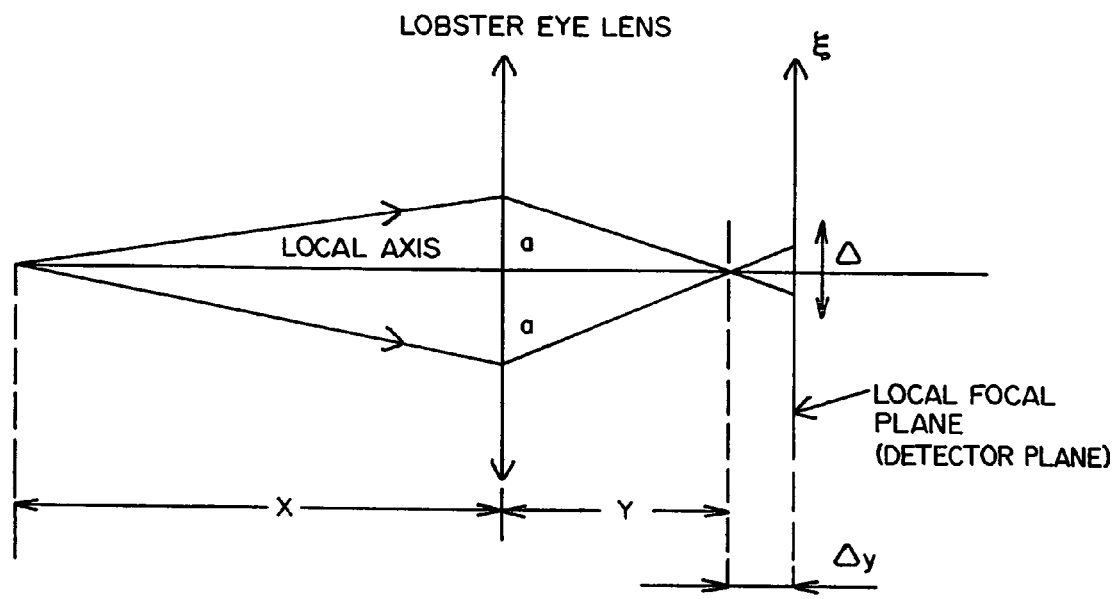
FIG. 3 is a local axis of lobster eye lens imaging system, shown for apodization purposes, in 1-D projection.
Figure 4:
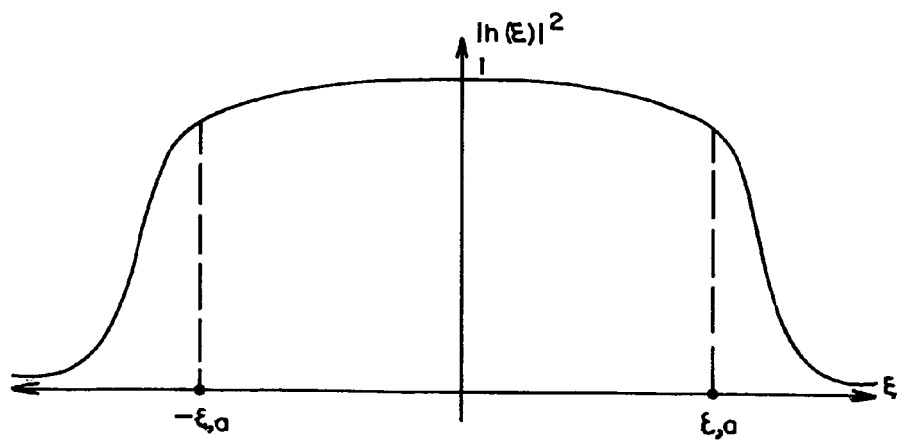
FIG. 4 is a 1D distribution module square of point response function, following Fresnel reflection distribution in the vicinity of total external reflection.

In the case of defocusing, or other geometric (Seidel) aberrations, we can compensate by applying apodization techniques. The general idea of apodization is explained in many books dealing with Fourier optics, the best known is Ref. [1], J. W. Goodman, "Introduction to Fourier Optics". The system of coordinates is illustrated in FIG. 3. In 1D projection, coordinate $\xi$—describes the location of defocusing spot, $\Delta$. Its profile follows Fresnel reflection in the vicinity of total external reflection (TEF). In practice, we have a multi-energetic X-ray beam; i.e., X-ray photons are not mono-energetic but have energy distribution. As a result, the profile of defocusing spot function, equivalent to a point response function, in the Fourier optics language, does not have sharp edges, as shown in FIG. 4.

In angular coordinates, $\xi_c$-position is equivalent to $\theta_c$-location, where $\theta_c$-TER cutoff-angle. From FIG. 1, we have $$2\xi_c = \Delta \quad (13)$$

From Fourier optics mathematical theory, for non-coherent systems, the module square of the point response function, $h(\xi)$, is inverse Fourier transform of the optical transfer function (OTF), in the form:

$$|h(\xi_x, \xi_y)|_2 = F_{-1}\{OTF(f_x, f_y)\} \quad (14)$$

where $(\xi_x, \xi_y)$—are coordinates of the local focal plane, in a general 2D-case; thus, for cutoff position:

$$\xi_x^2 + \xi_y^2 = \xi_c^2 = \left(\frac{\Delta^2}{2}\right), \quad (15)$$

and $$OTF(f_x, f_y) = \hat{F}\{|h(\xi_x + \xi_y)|^2\} \quad (16)$$

$$= \frac{\int_-^+ \int_-^\infty |\tilde{h}(\xi_x + \xi_y)|^2 \exp\{-i2\pi(fx \cdot \xi x + fy \cdot \xi y)\} d\xi_x d\xi_y}{\int\int |h(\xi_x, \xi_y)|^2 d\xi_x d\xi_y}$$

where $h(\xi_x, \xi_y)$—is the normalized point response function.

Figure 5:
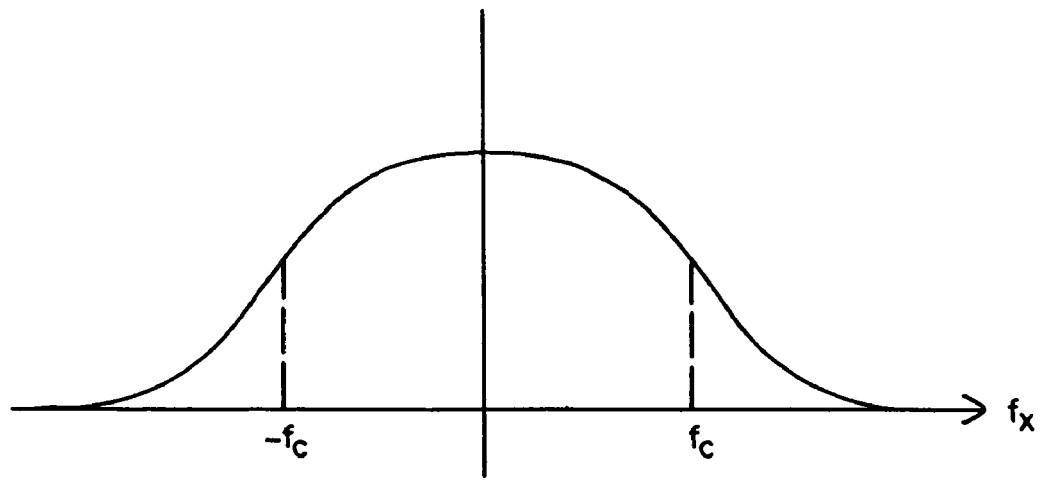
FIG. 5 is a 1D distribution of module of the optical transfer function.

Further details can be found in Goodman's Introduction to Fourier Optics. The module of the OTF, or $|OTF(f_x, f_y)|$ is called modulation transfer function (MTF). The apodization operation is provided by the following relation:

$$\hat{I}_g(f_x, f_y) = (\hat{OTF})^{-1}(f_x, f_y)\hat{I}_i(f_x, f_y) \quad (17)$$

where $\hat{I}_g(f_x, f_y)$ is the 2D Fourier transform, as in Equation (16), of the normalized object geometric intensity distribution, while $\hat{I}_i(f_x, f_y)$ is that of image geometric intensity distribution, which is convolved with the point response as in FIG. 2. Because the $|h(\xi_x, f_y)|_2$ is a smooth function of $(\xi_x, f_y)$—coordinates, its 2D-Fourier transform is also a smooth function of $(f_x, f_y)$—spatial frequency coordinates, such that the spatial frequency cutoff value, $f_c$, is $$f_c = \frac{1}{\xi_c} \quad (18)$$

as shown in FIG. 5.

In order to provide effective apodization, we need to provide a numerical calculation of formula (5) where $I_i(\xi_x, \xi_y)$—image intensity distribution, measured at local focal plane, while $h(\xi_x, f_y)$—can be computed analytically from Fresnel reflection distribution in the vicinity of the ETR. Then, $\hat{I}_i(f_x, f_y)$—is computed by fast Fourier transform (FFT) from $I_i$, and Equation (17) is numerically computed to calculate $\hat{I}_g(f_x, f_y)$ as object intensity distribution, with canceled defocusing effect. This type of apodization is different from that for regular optical systems which apply rather artificial apodization functions in a Fourier plane. Here, the apodization function has a natural form, obtained from physical angular distribution of the Fresnel reflection coefficient. This new method of apodization is very effective because the |OTF|=MTF does not have zeros except at infinity; thus, the inverse operation (5) is well-defined.

Figure 6:
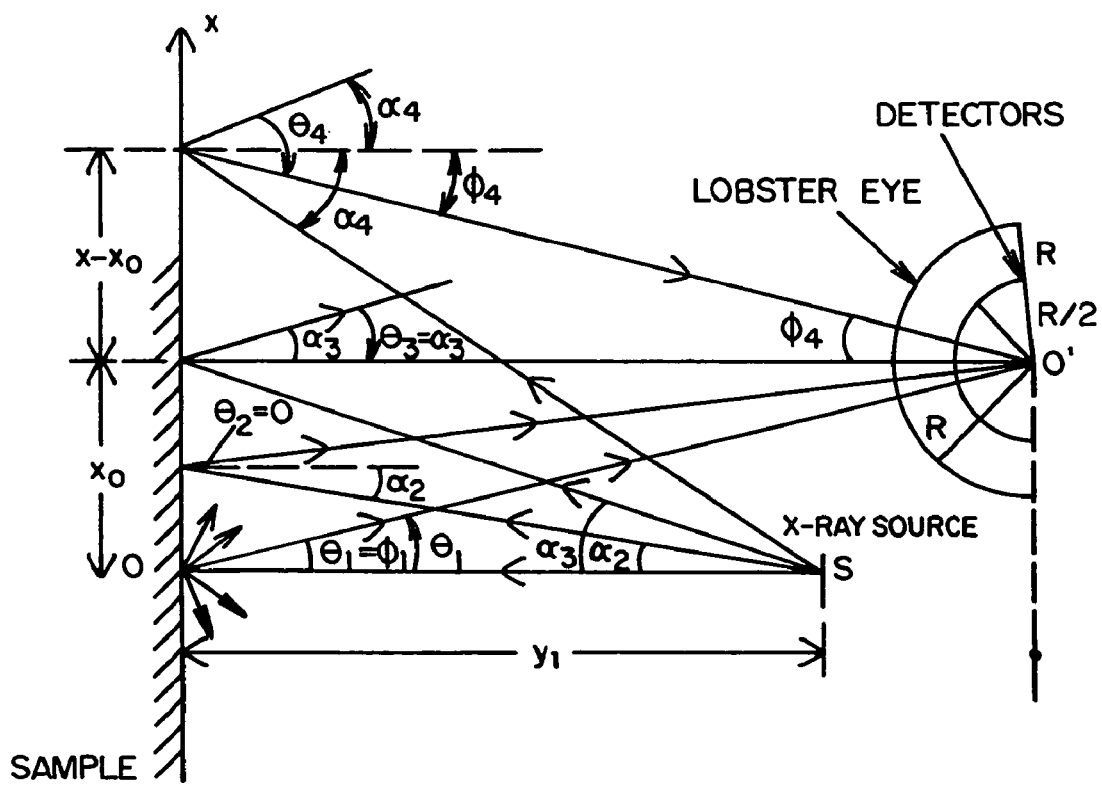
FIG. 6 is a 1D geometry of the X-ray source, a sample, and lobster eye lens.

The other type of canceling of defocusing effect is, simply, by mechanical zooming; i.e., zeroing of $\Delta y$-value, by movement of the detector plane, as in FIG. 6. Still further, a complementary method is to compensate for the field curvature of the focal surface, since the local focal plane, as in FIG. 1, is only locally plane.

X-Ray Angular Spectrometer

Figure 7:
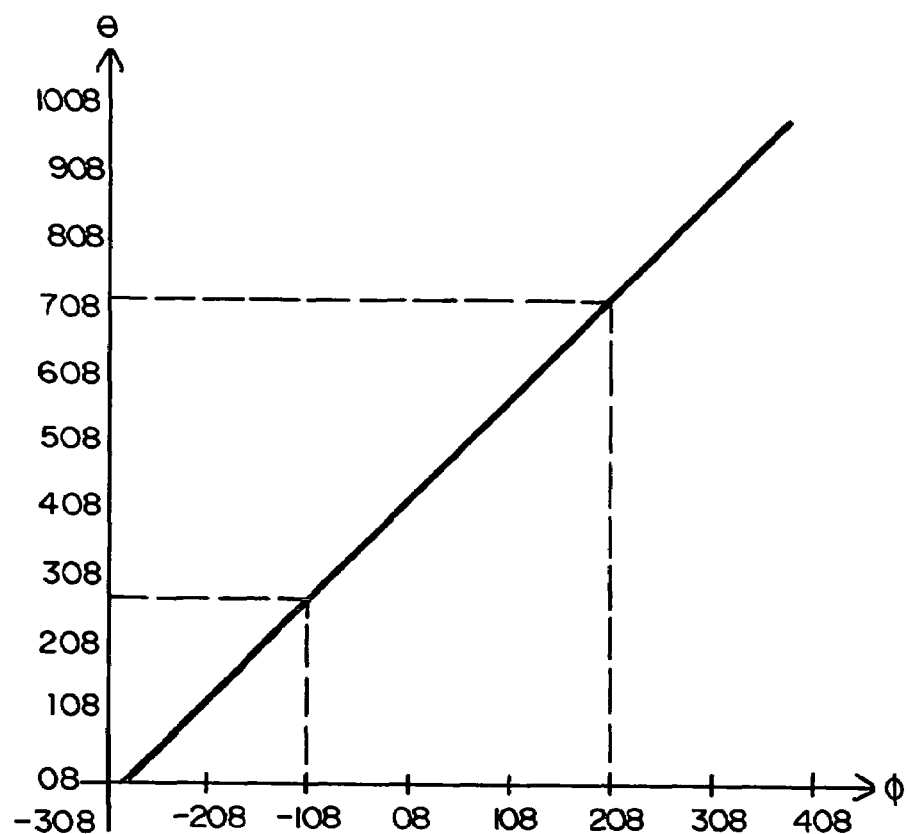
FIG. 7 is a graph showing the dependence of scattering angle, θ, as a function of detector position of angle φ, for Equations (21 and 22)

The specific geometry of an X-ray source, a sample, and a lobster eye lens defines scattering angles of X-rays reflected from the sample. The scattering angle, $\theta$, is defined as angular departure from specular reflection, as shown in FIG. 6. The X-ray conical beam, generated by the source, S, in the form of a bundle of X-rays, incident at the sample, defined in 1D projection by axis-x, is reflected (back-scattered) from the sample, into the lobster eye lens. Each X-ray is defined by the incidence angle $\alpha$ and the specular reflection angle, also $\alpha$. The back-scattered X-ray is expanded into a cone, centered around a specular reflection. The scattered cone, as a bundle of scattered X-rays, is defined by a specific scattering cross-section, depending on a type of chemical component or material of a sample, mostly defined by its Z-number. The higher the Z-number, the narrower the scattering cone. One ray is directed into a center of the lobster eye lens, 0', and is received by a detector, located at the lobster eye hemisphere, with radius, R/2, with its angular position, $\phi$. Therefore, there exists some relation between, $\alpha$, $\phi$, and $\theta$, obtained from FIG. 6, in the form of three equations:

$$x - x_0 = y_0 \tan\phi \quad (19a)$$

$$x = y_1 \tan\alpha \quad (19b)$$

$$\alpha + \phi = \theta \quad (19c)$$

with three unknowns: $\alpha$, $\phi$, $\theta$. Eliminating them, and introducing: $u = \tan\theta$, and $v = \tan\phi$, we obtain $$u = \frac{x_o + v(y_0 + y_1)}{y_1 - vx_o - v^2 y_o} \quad (20)$$

which for $x_o = y_o = y_1$, becomes $$u = \frac{1 + 2v}{1 - v - v^2} \quad (21)$$

where $u=0$, for $v=\frac{1}{2}$, and $\phi=26.6°$; then $\theta_2=0$, as shown in FIG. 1; while $u=\infty$, for $v=(-1+\sqrt{5})/2$, or, $\phi=31.7°$. Also, for $v=0$, $u=1$, and $\theta_3=45°=\gamma_3$. We see that for $x=0$, $\theta<0$; then $\theta\theta_2=0$; then, $\theta>0$; i.e., $\theta$-angle is a monotonic almost straight line function of $\phi$, as shown in FIG. 7, for Equation (21).

We see that the relation:

$$\theta = \theta(\phi) \quad (22)$$

is almost linear, with an approximate inclination coefficient:

$$K = \frac{\Delta\theta}{\Delta\phi} = 1.5 \qquad (23)$$

Figure 8:
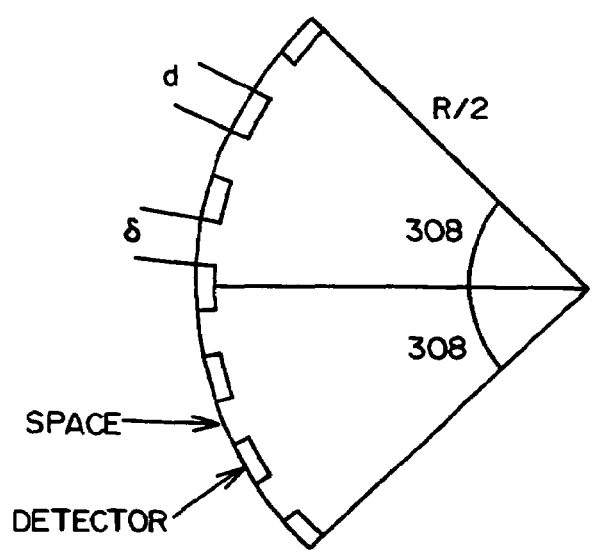
FIG. 8 is a drawing of a lobster eye detector array cross-section, with conical angle 60°.

Therefore, in one stroke (or flash), we can obtain the full angular characteristics of the sample which justifies the name "angular starring spectrometer." For a lobster eye lens with a conical angle of 60°, or π/3, as shown in FIG. 8, detectors have sizes, δ, and space, d, so duty cycle is d/δ. Assuming an angular resolution of 1°, the number of detectors is N=60, and distance between detectors, or pixel size, is δ+d=26 mm/60=433 μm, divided as 303/130, for duty cycle 70/30. Assume R=5 cm, and x=1 m; then, transversal magnification is $Mt_c$=¹⁄₄₁, and for image resolution of 433 μm, we obtain an object resolution of 1.77 cm, or 3.9 mm, for R=5 cm, and x=20 cm.

Figure 9:
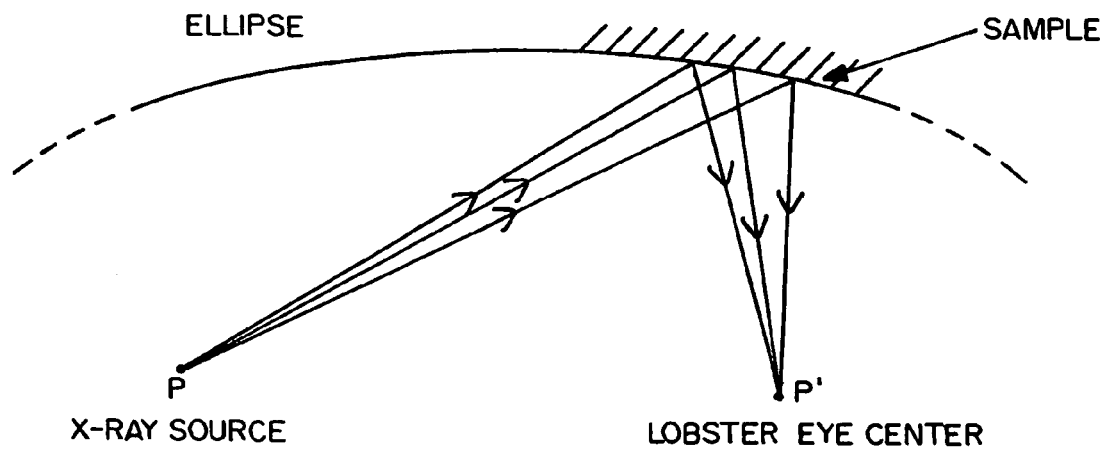
FIG. 9 is a drawing showing the specific geometry for X-ray source and lobster eye center for θ=0 where the sample surface is the ellipse of the revolution around PP'-axis, where PP' are ellipse foci.
Figure 10:
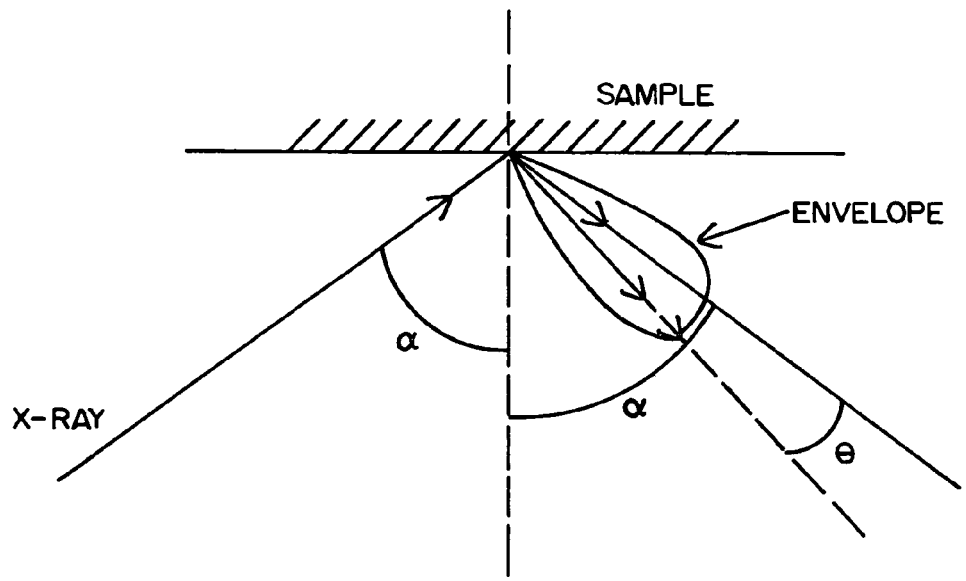
FIG. 10 is a drawing showing the geometry of scattering angle.

The plane sample geometry, as in FIG. 6, allows for monotonic, almost linear θ(φ)—relation, as in FIG. 7. In contrast, if we would like to always obtain θ=0, for any point at a sample, we need to make a sample's surface profile in the form of the ellipse of the revolution, as shown in FIG. 9, where P, and P' are ellipse focii, and the ellipse curve should be rotated around the ππ' axis.

Calibration

The envelope of scattering angles, θ, is around specular reflection angle, α. Such an envelope, in general, depends on α. Otherwise, the system is called, using Fourier language, angle-invariant optics. Even if the system is angle-variant, the angle variance can almost be the same within a category of samples. In such an approximation, we can develop a universal calibration procedure which allows us to calibrate all geometrical factors, such as source distance, sample distance, and lobster eye distance. In such a case, the general measurement formula has the following form:

$$I(\theta) = M(\theta)I_o(\theta) \qquad (24)$$

where $I_o(\theta)$, the intensity of the incident X-ray beam, depends on all geometrical factors (and is difficult to analyze), and M(θ) is unknown angular characteristics of a sample, to be separated from $I_o(\theta)$. Instead of separating it analytically, however, we develop a calibration curve in the form:

$$I_c(\theta) = M_c(\theta)I_o(\theta) \qquad (25)$$

where $M_c(\theta)$ is an angular characteristic of a known sample used for calibration, and $I_c(\theta)$ is the measured detector intensity for this sample through the known angular curve (as shown in FIG. 7). Dividing Equation (24) by Equation (25), we obtain the calibration formula:

$$M(\theta) = M_c(\theta) \underset{\underset{\text{to be found}}{\uparrow}}{\frac{\overset{\text{measured}}{\overset{\downarrow}{I(\theta)}}}{\underset{\underset{\text{calibration curve, known}}{\uparrow}}{I_o(\theta)}}} \qquad (26)$$

We can easily generalize this formula for full 3D geometry. This formula can be applied in at least two ways:
1. For Angular Spectroscopy
2. For Contrast-Enhanced Imagery The first case is discussed above; the second case can be explained as follows. Consider the geometry of an object (a sample), as in FIG. 11. Higher x-values equal higher θ-angles; thus, if we locate an object, at position, characterized by high positive x-values, or high positive φ-values, the image of such an object will be responsive only to such object elements that have low Z-numbers, leading to contrast enhancement of such an object.

Time Gating and X-Ray Staring Imaging

Figure 11:
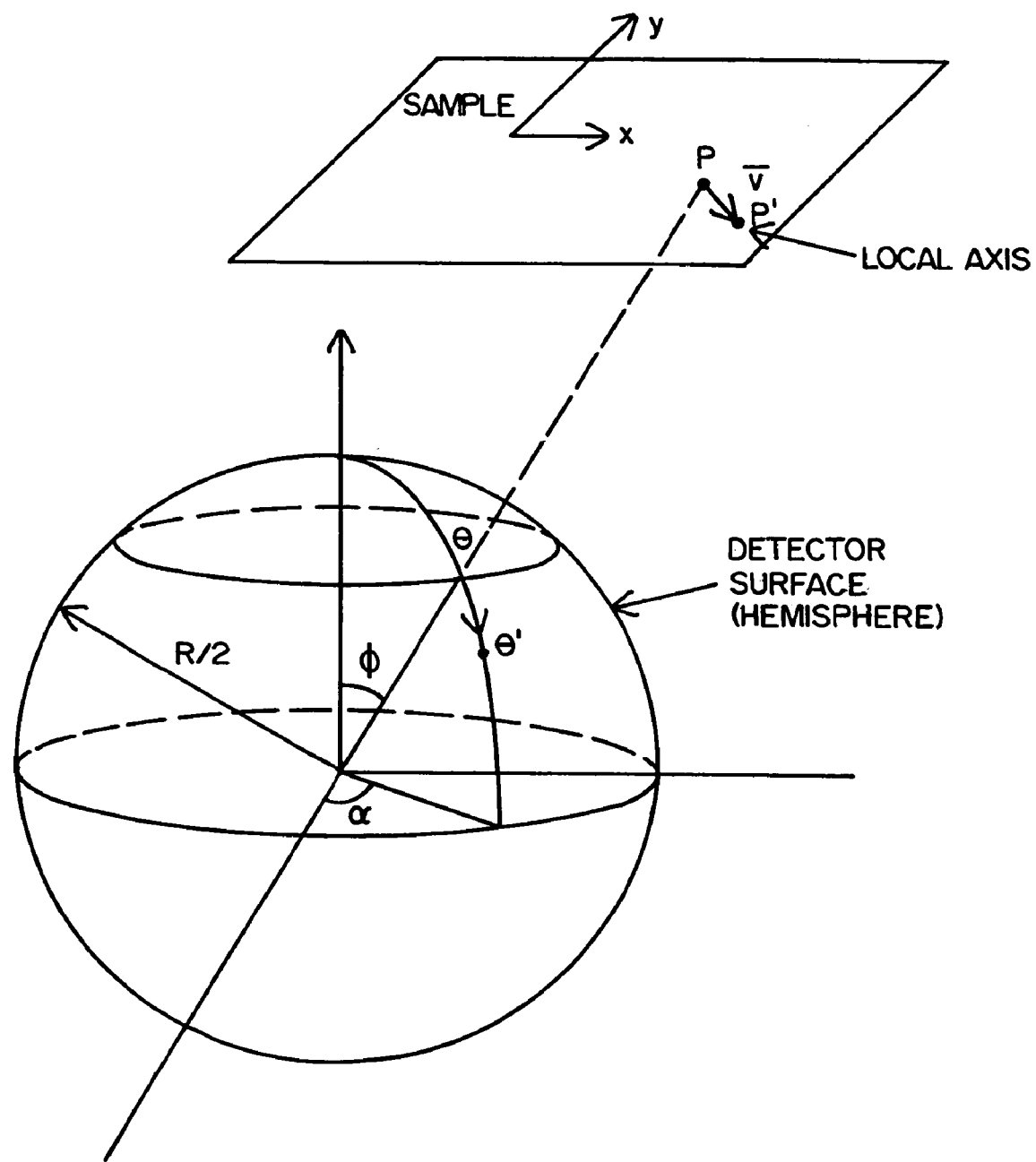
FIG. 11 is a 3D geometrical configuration of the lobster eye detector and the object.

The lobster eye detector surface is located on a hemisphere with radius R/2, where R—Lobster Eye lens radius. Each point of this surface, Q, has its equivalent point, P, located at the X-ray sample as shown in FIG. 11.

The point, θ, has spherical coordinates (ρ,φ) and its equivalent, P, has Cartezian coordinates (x,y). When point P moves at speed v, as shown in FIG. 11, its equivalent Q, also moves to point Q'. Assuming speed v, point P, moves a distance vt, during time, t. For the specific hard x-ray case, if X-ray "hits" point P, the multi-scattering inside the sample occurs, especially for small Z-numbers, yielding PP'-shift. Using lobster eye imaging equation, the distance PP':

$$PP' = vt \qquad (27)$$

is reduced to $$\frac{PP'}{M_t} = \frac{vt}{M_t} \qquad (28)$$

where $M_t$—is transversal magnification. For R=6 cm, and x=1 m, we obtain $$M_t = \frac{1}{41}.$$

Assuming the detector pixel size of 100 μm, the equivalent size in object plane, is 4.1 mm, which is a realistic value, since even 1 cm-shifts are possible. The time delay between lobster eye and the samples for x=l=1 m, is (v=c):

$$\Delta t_o = \frac{2\ell}{c} = \frac{200 \text{cm}}{3 \cdot 10^{10} \text{cm/sec}} = 6.6 n\text{sec} \qquad (29)$$

Figure 12:
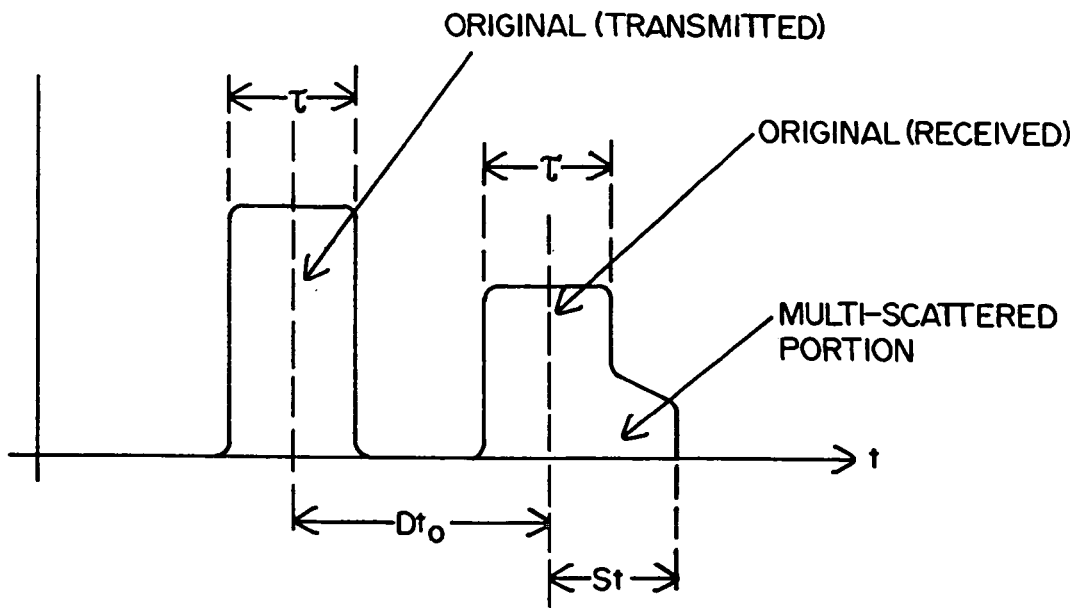
FIG. 12 is a time-line of the X-ray pulse transmitted to the object and received pulse of backscattered X-rays including multi-scattered portion.

Therefore, the pulse duration τ, must be smaller than 6.6 ns for such distances, as shown in FIG. 12.

FIG. 12 shows two pulses, the original transmitted one, and the original received one, the latter one, including multi-scatter portion. By measuring δt, we can reason about the nature of the sample such as organic or nonorganic, air, metal, etc. Of course, we need to send many such pulses in equal intervals, $\Delta t_o$, to obtain a synthetic image. Lower Z-number, larger temporal shift value of δt. The time gating can be complementary to angular multiplexing:

$$\delta x = c\delta\tau \qquad (30)$$

where v≅c=3·10¹⁰ cm/s, and δx—is spatial shift due to multi-scattering.

General Properties of X-Rays

Figure 13:
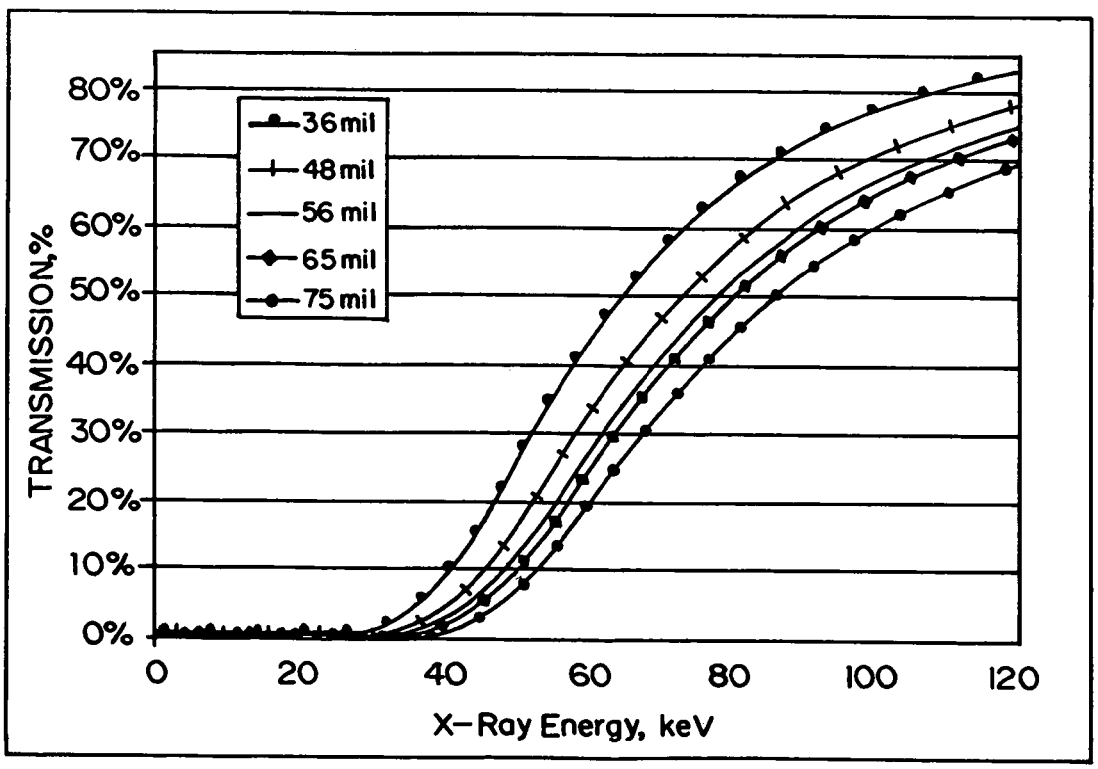
FIG. 13 is a graph of calculated X-ray transmission of steel metal sheets 36 mil, 48 mil, 56 mil, 65 mil and 75 mil thick as a function of X-ray energy.

It is commonly believed that X-rays easily penetrate soft materials such as human tissues and organic polymers, producing "density shadowgram" X-ray images. Another common belief is that X-rays cannot penetrate metal. Neither statement is correct. X-rays photons are scattered widely by interaction with soft nonmetal substances, and some of them are scattered back toward the X-ray source. Such photons are called ballistic backscattered photons. At the same time, 18% of X-ray photons with an average energy of 60 keV (or wavelength $\lambda$=0.2 Å) penetrate a 56 mil steel sheet (see FIG. 13). X-rays with energies of 60 keV and higher are used for routine chest X-rays.

Current Capillary X-Ray Focusing Optics

The nature of X-rays prohibits creation of refractive focusing elements for them. The only possible way to work with X-rays is to use their reflections from smooth metal surfaces under small grazing angles of incidence. Classical X-ray reflection optics are heavy, bulky (meter scale), expensive, and hard to align. This has led to the development of Kumakov X-ray focusing optics, based on long, curved, circular capillaries[2, 3]. Because of the very small critical grazing angles ($\leq$3.6 arc-minutes for 60 keV X-rays), and relatively large inner capillary diameters, the capillaries have to be enormously long.

In addition, the significant thickness of capillary elements and dead space between them considerably reduces the fill factor of Kumakov X-ray optics. The more advanced LE-type focusing X-ray optics is based on glass slumped microchannel plates (MCPs). However, the spectral range of operation of existing LE optics is limited to X-rays with energies $\leq$4 keV (or $\lambda$=3.1 Å)[4-6]. Harder X-rays with smaller critical grazing angles cannot be focused efficiently by glass MCPs because of the small length-to-width ratio (aspect ratio) of their channels[4-8].

Lobster Eye X-Ray Focusing Optics

A lobster views the world through an array of box-like square-cross-section ommatidia (eyelets) curved across the outside of its eye.

In crustacean eyes, the cells are short and rectangular, about twice as long as they are wide. Light is reflected over a wide range of angles of incidence to form a rather fast focus. For hard X-ray applications, the cell length must be about 100s times the width, but the optical principle remains the same as that in the eye of the crustacean. It is closely related to Schmidt's two-dimensional device, except that merging the two orthogonal sets of plates and adopting spherical rather than cylindrical symmetry removes the preferred axis, and the field-of-view (FOV) can be as large as desired. The eye of a lobster, for example, has an FOV of slightly more than 180°.

Figure 14A:
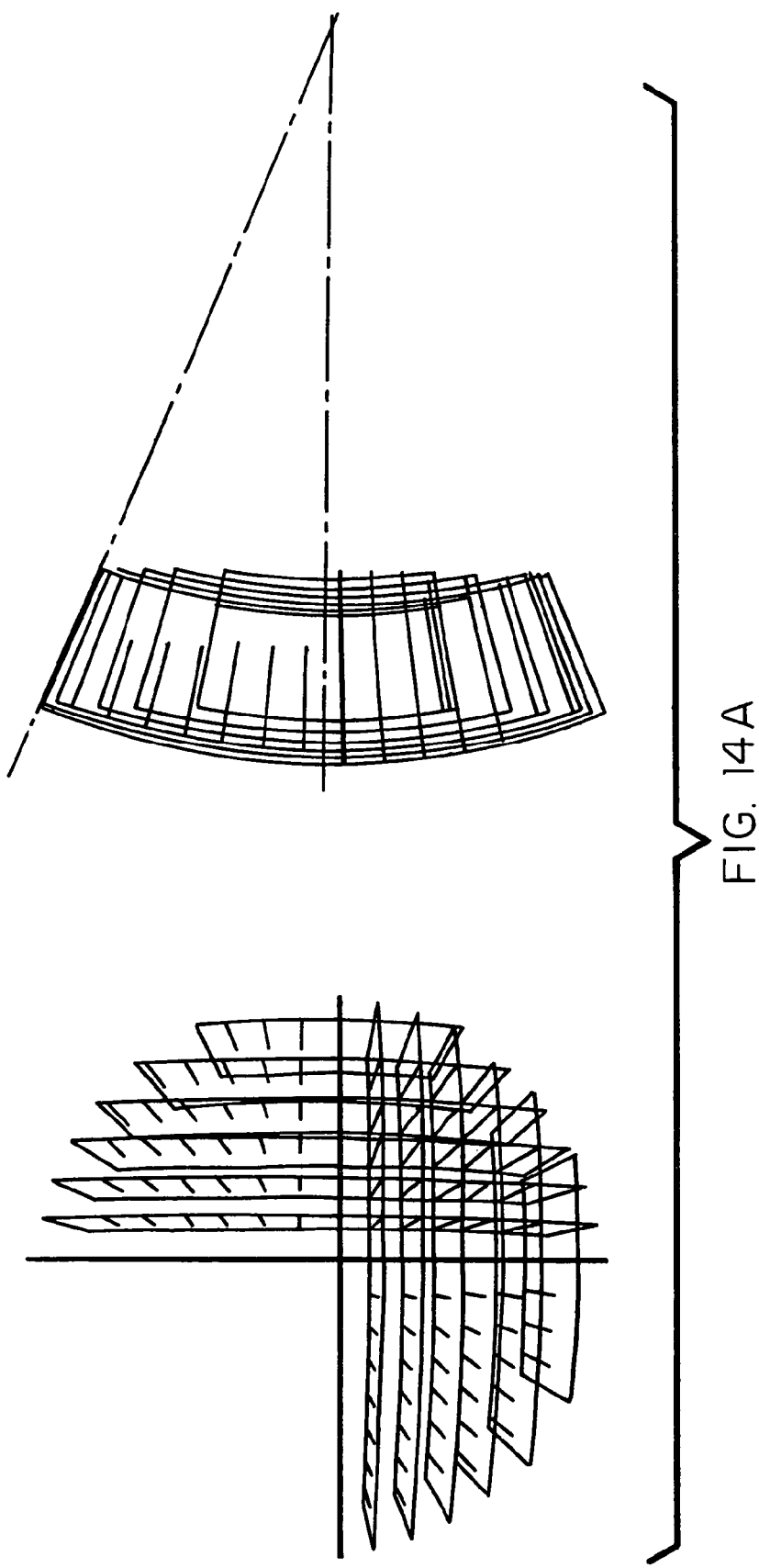
FIG. 14, consisting of FIGS. 14A and 14B, is a drawing and photograph of a unique lobster eye structure used in the preferred embodiment.
Figure 14B:
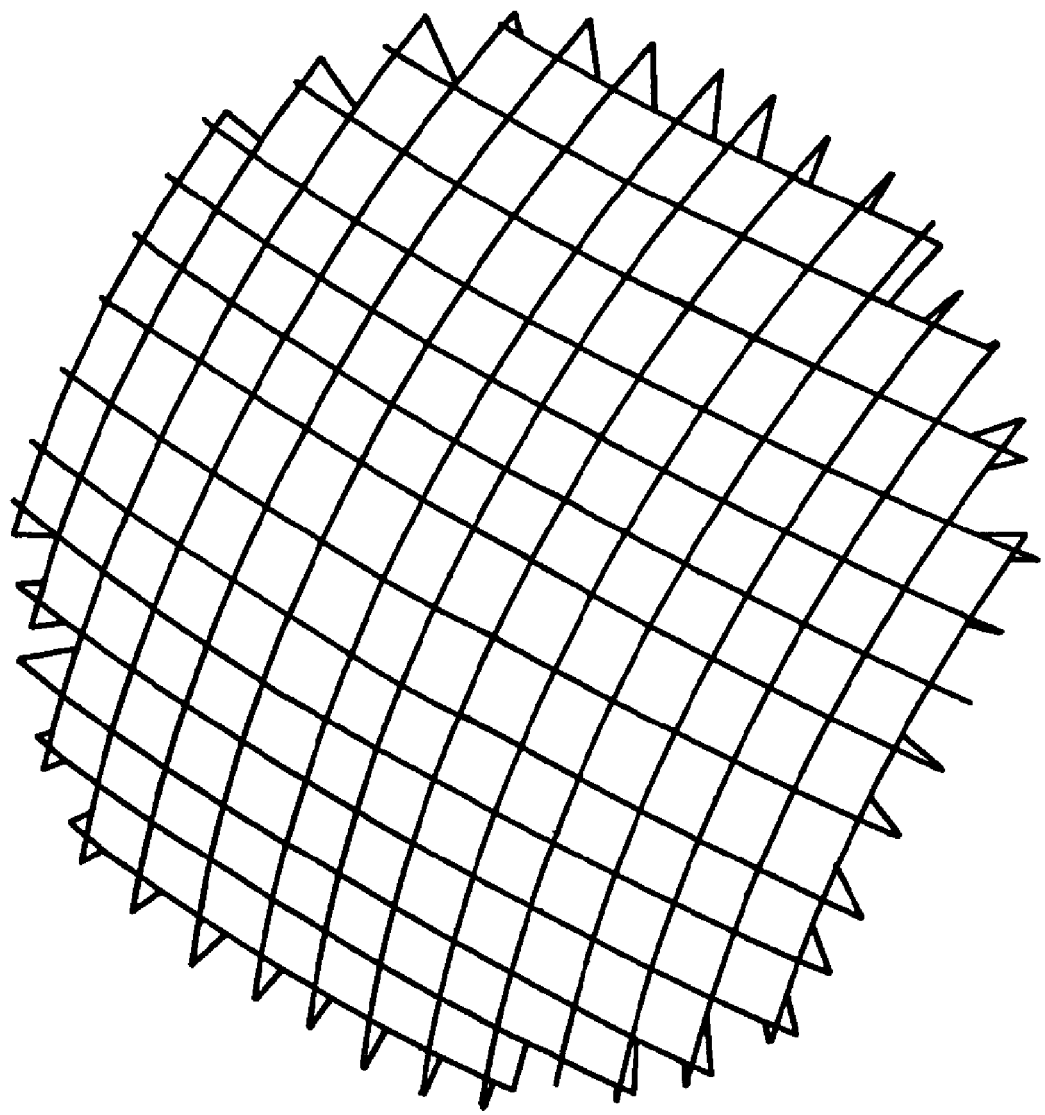

Each ommatidium captures a small amount of light, which comes to the eye from all angles, and the light from numerous ommatidia is focused to form an image. Physicists at Physical Optics Corporation have copied this structure in long, hollow metal microchannels organized in a LE structure to focus hard X-rays[9] see (FIGS. 14A and 14B).

Figure 15:
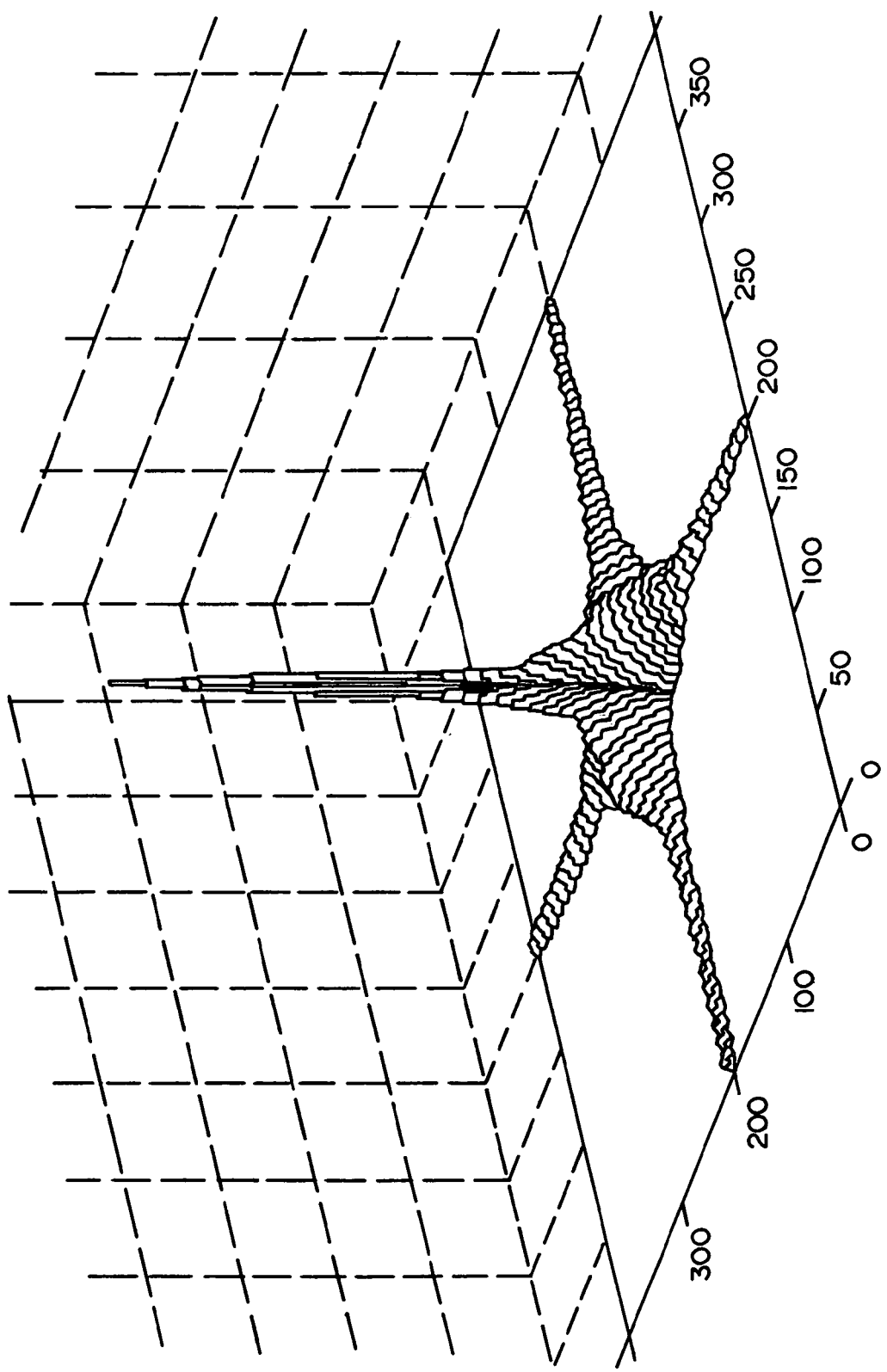
FIG. 15 is a graph of calculated intensity distribution in the focal plane of the lobster eye optics.

In LE geometry, it is possible to arrange for X-ray reflections to occur at very low angles. At angles of less than 12 arc-minutes, the reflectivity of gold film, for example, is high; as a result, little incident flux is lost. FIG. 15 illustrates parallel X-rays with a small grazing angle reflected (focused) on the same cross-shaped spot. Initially, X-rays strike an array of square, long hollow cells, and converge on a common point, focusing the X-rays onto that single point. An X-ray that enters any single element-cell, shaped like a square tunnel, bounces off two reflecting walls and emerges parallel to the beams emerging from adjacent cells. The intensity in the central region of the spot of the reflected parallel X-ray flux can be thousands of times greater than that of the incident X-ray flux. As a true focusing device, the LE optics can image objects effectively against a diffuse background and thereby improve observation of faint objects.

With an odd number of reflections, usually one or three, the X-ray passes straight to the focal surface on the detector. X-rays that reflect off two orthogonal walls are sent to a common focal spot. Those that hit only one wall end up on a line, and the remainder pass straight through, as depicted in FIG. 15. Rays reflected an even number of times, including rays that pass with no reflection, contribute to background noise.

X-Ray Backscattering from Plastic and Metals.

When the Lobster Eye X-ray Imaging System X-ray generator irradiates an object underwater (130 kVp (kilovolt peak energy) to 180 kVp x-ray spectra with mean X-ray energies from 40 to 120 keV (or wavelength $\lambda$=0.31 to 0.1 Å), it produces two significant interactions: (i) Compton scattering and (ii) the photoelectric effect[10, 11]. Materials with different average local atomic numbers (Z numbers) and different electron densities have different intensity values in the Compton scattering images[12]. The relative probability of these interactions is a function of Z number and electron density of the material. In the photoelectric effect, an x-ray photon is absorbed, and an electron is emitted. For an X-ray photon energy of about 60 keV (0.2 Å) or lower, the higher Z number materials have higher photoelectric cross sections and lower Compton scatter cross sections. For low-Z materials, it is just the opposite. In materials with high Z numbers, such as metals, the bulk of the X-ray illumination photons are absorbed by the material through the photoelectric effect, and few photons are scattered via the Compton interaction.

Figure 16:
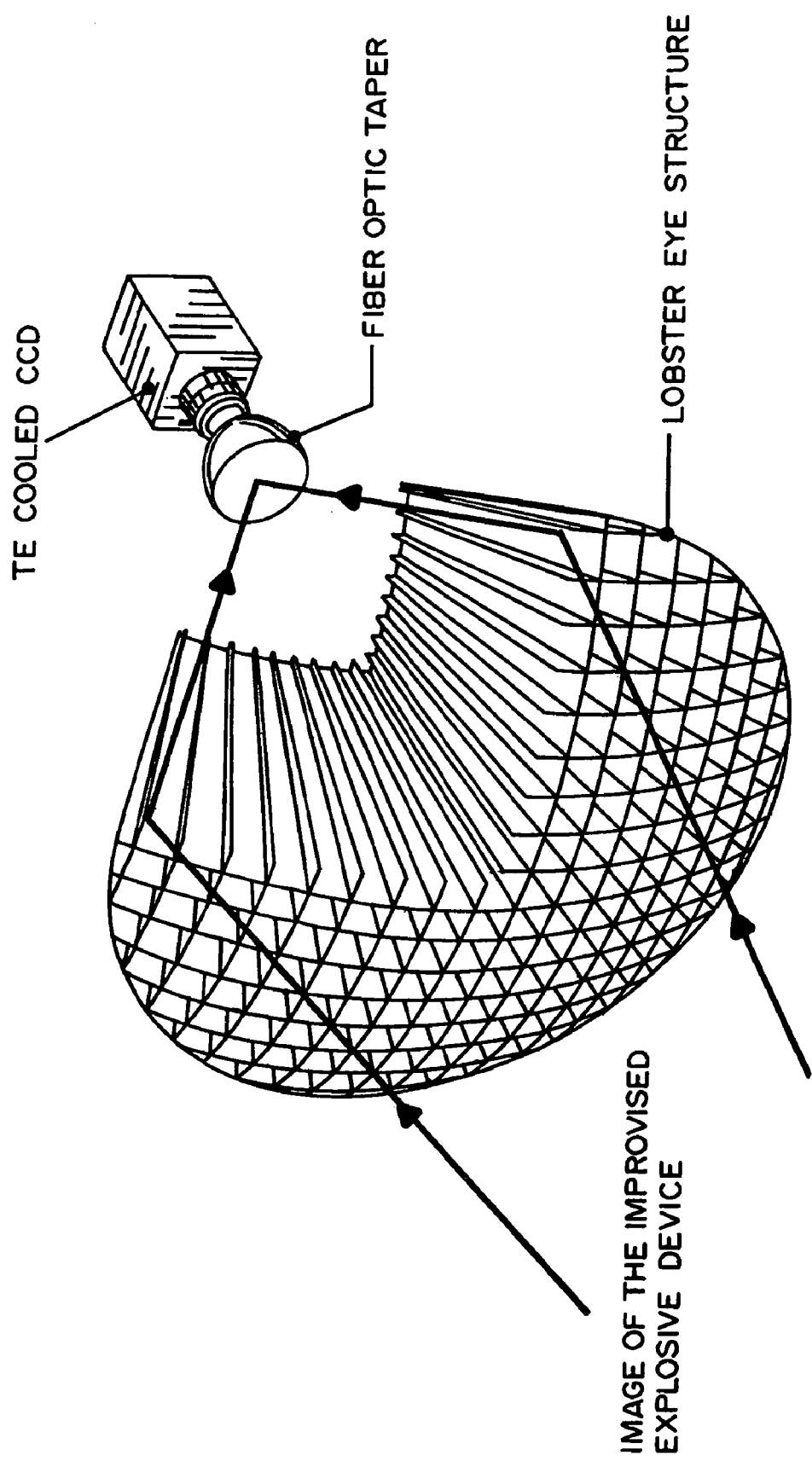
FIG. 16 is an artist's conceptual illustration of a detection module of the starting imaging X-ray inspection system.

Thus, metallic materials will have low intensity values in the Staring Imaging X-ray Inspection System images. In contrast, materials such as plastic have a lower Z number and medium electron density. When plastic is imaged by the Staring Imaging X-ray Inspection System, many X-ray illumination photons have Compton interactions, and some of the photons are backscattered to and registered by the LE detector, which includes LE optics focusing X-rays to the scintillating screen coupled to the cooled CCD camera (see FIG. 16). Thus, in Compton backscattering imaging (CBI), a low-Z material is represented by a high-intensity value of backscattered X-ray photons.

Current Backscattering Techniques

State-of-the-art X-ray Compton backscatter imaging (CBI) techniques[11-14] such as lateral migration radiography (LMR)[10,11] can image the surface, subsurface, or internal structure of soils to detect landmines. LMR systems have separate detectors for imaging single-backscattered X-ray photons (SBPs), which collide with an object's atoms only once, and multiple-backscattered photons (MBPs) for object interrogation. Because the number of SBPs and MBPs is generally low, and there is some geometric overlap, the two images have poor signal-to-noise ratio (SNR) and resolution, and severe geometric distortion. LMR (as well as all other CBI techniques) cannot focus hard X-rays. Building an X-ray image relies on a scanning pencil beam of X-rays and an expensive, bulky, large-area X-ray detector with photomultiplier tubes (PMTs). Resolution, contrast, FOV, and SNR of LMR are limited by the intensity, size, and speed of the scanning pencil beam. LMR has a low acquisition rate, limited to 1 m²/min. [11-12, 14], and a long and complicated image reconstruction process. Generation of a scanning pencil beam is inefficient; it uses only 0.01% of generated X-rays and requires heavy, lead, fast-rotating chopper wheels or rotating collimators with large moments of inertia. Therefore, state-of-the-art X-ray backscatter systems do not meet requirements for detection of, for example, buried mines.

Staring Digital X-Ray Imaging Detector

An embodiment of a staring digital detector for a Staring Imaging X-ray Inspection System includes a microchannel plate (MCP), micromachined from a silicon wafer and slumped into a semispherical shape coinciding with the semispherical focal surface of the Lobster Eye X-ray focusing optics. The size, shape, and position of the microchannels of the silicon MCP are determined by a photolithographic method, and will provide a high, >85%, fill factor.

Existing lead-glass MCPs are high-cost, heavy, limited in area, and rigid, and do not preserve the periodicity of the microchannels or their wall smoothness. This latter causes a significant degradation of focusing performance, which determined, actually, by the geometry of the MCP structure and the surface roughness of the channel walls[6, 15].

In contrast to SOTA lead-glass MCPs, silicon MCPs are low-cost, light, large in area, and mechanically stable. They will be fabricated by electrochemical anisotropic etching (ECANE) of silicon wafers, and they will then slump into the desirable spherical shape. The high-aspect ratio microchannels will be filled with scintillating a material like NaI or CsI(Tl) that is efficient for hard X-rays.

The fabrication of MCPs for this Staring Digital Detector (SDD), and the accompanying micromachining and slumping technology will include the following steps:

(1) Pore size, shape, and position within an array will be determined by a photolithographic method. Pores will then be etched anisotropically through a Si-monocrystalline substrate wafer.

(2) A micromachined Si MCP will be slumped in to the desired spherical shape by a special thermocycling process, combined with oxidizing the pore walls.

(3) Pores metallization will be achieved by chemical vacuum deposition (CVD) growth to form continuous, smooth, X-ray-reflecting pore walls. The $SiO_2$ layer of the walls will allow the use of a large variety of metals having high z-numbers (in contrast to glass MCP technology technology).

(4) SDD will be manufactured from commonly available, inexpensive, monocrystalline Si wafers measuring more than 150 mm (6 in.) in diameter.

(5) Melting the scintillating material into the microchannels of slumped silicon MCPs in a vacuum based on the fact that the melting temperature of silicon is >1400° C., which is almost twice as high as that of scintillating materials such as NaI or CsI(Tl).

Figure 17:
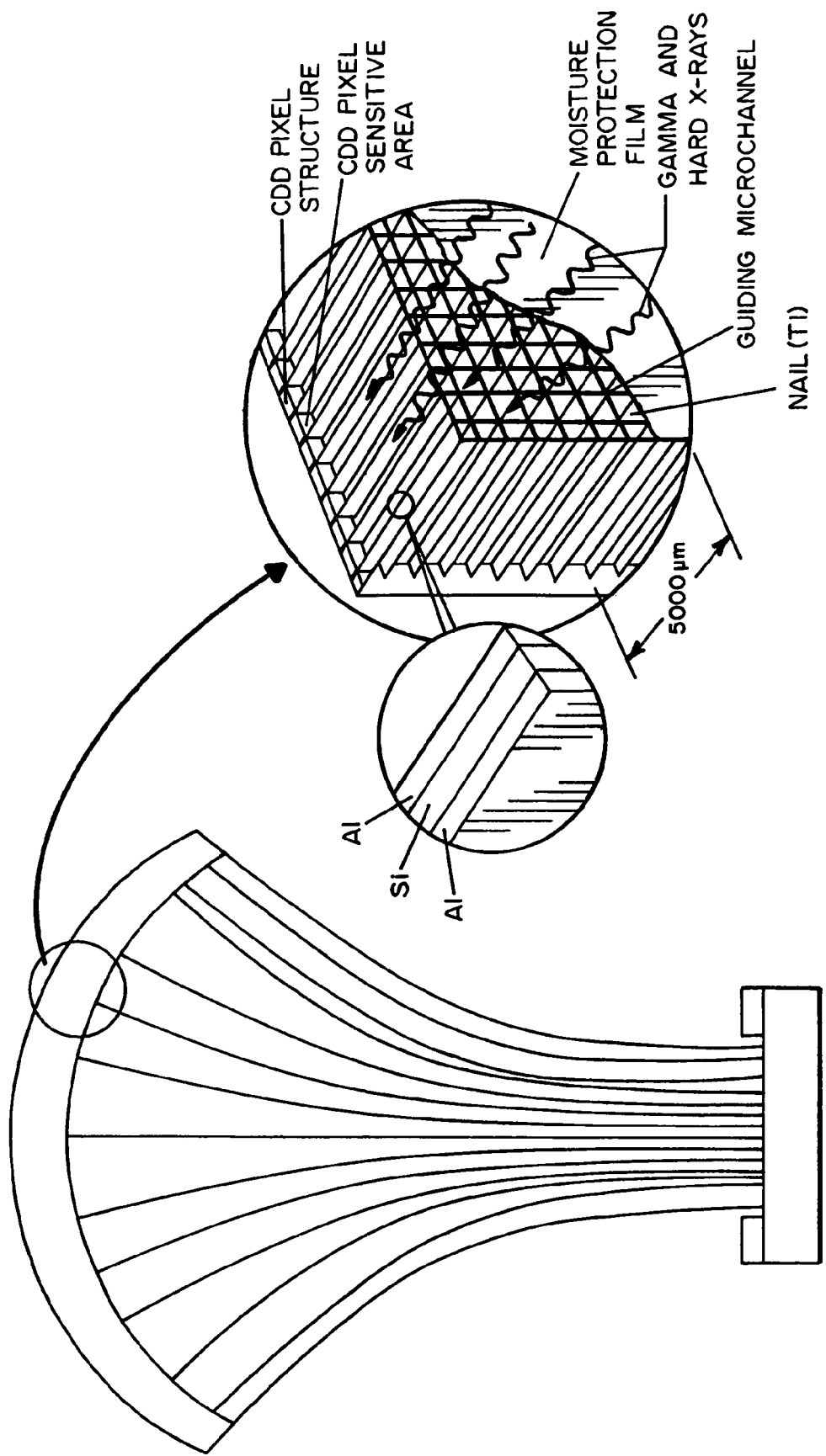
FIG. 17 is a drawing of the structure and operating principle of the Staring Digital Detector (SDD)

FIG. 17 illustrates the structure and operating principle of the SDD system. The SDD will be based on a microchannel guide structure for signal readout, coupled with a state-of-the-art full-frame CCD through the fiber optical taper. The input surface of the fiber optical taper has a semispherical shape and coincides with the semispherical focal surface of the Lobster Eye X-ray focusing optics. The output surface of the taper is flat and is attached to the CCD matrix. The SDD will contain high-aspect-ratio guiding microchannels with >85% fill factor, in which the walls are covered with a reflecting aluminum layer and filled, for example, with sodium iodide scintillating material. This material absorbs hard X-ray photons with a quantum efficiency of >90%, and converts them into visible light. As a result, an Al-clad NaI(Tl) core is a high-aspect-ratio optical conduit structure, which will deliver a flash of scintillating light bright enough (concentrated in a very small area of the microchannel cross section of a few hundred square microns) to be detected by a CCD array at room temperature, identifying the energy content of X-ray radiation with high accuracy.

The intensity of visible light sparks generated in NaI (Tl) is proportional to their energy at a ratio of ~4,000 visible light photons per 100 keV photon. The attenuation length of NaI(Tl), for example, for 60 keV photons (wavelength $\lambda$=0.2 Å) is 0.5 mm; for 100 keV photons (wavelength $\lambda$=0.12 Å) it is 1.8 mm.

The light emitted by the NaI(Tl) scintillator within a microchannel goes to a sensitive area of corresponding CCD pixels with no losses or crosstalk among pixels, similar to fiber optic light conduits. At the end of the exposure, the charge in the active region of the CCD will be quickly (~40 ms) transferred into frame storage. In this way, the SDD will perform photon counting and energy discrimination. To discriminate the energy of X-ray photons, the CCD of the SDD must register frames at a high rate so that only a few events will be registered in each frame, and the intensity of each spark in the scintillator can be measured separately.

Fabrication of X-Ray Focusing Optics for Lobster Eye X-Ray Imaging System

In the current invention, all polishing and finishing is performed on "flat" parts of X-ray Lobster Eye during a time when they are easily accessible while in the majority of prior art these activities cannot be performed due to poor accessibility. The polishing and finishing activities necessary to achieve the high surface flatness and low surface roughness critical to the formation of a high-performance X-ray Lobster Eye are achieved due to the complete accessibility of all material surfaces during the initial fabrication of the current invention.

For example, in most prior art, "corners" are difficult to impossible to access for polishing and finishing, while perfectly polished and finished 90-degree corners necessary for hard X-ray optics are inherent in the design of the current invention—and are automatically achieved during the final assembly process of the novel Lobster Eye.

In previous prior art[4-6], it seems on the surface to be the same, but a critical "half-step" is missing—the decussate (crisscross) arrangement or interleaving of the two separate horizontal and vertical layers into a single three-dimensional meshed structure, which forms a lobster eye lens, as is the case with the current invention.

In the current invention, tapered trapezoidal channels are formed three-dimensionally by continuously diminishing square cross-sections, achieving the "ideal" Lobster Eye form factor.

It should be emphasized that this invention is not "creating" the Lobster Eye shape, but rather "making" the Lobster Eye shape, while preserving the strict requirements of X-ray optics.

The result of the novel and unique fabrication and assembly process embodied in this invention results in a Lobster Eye structure of high geometrical precision and surface perfection required to successfully fabricate X-Ray mirrors.

Figure 18:
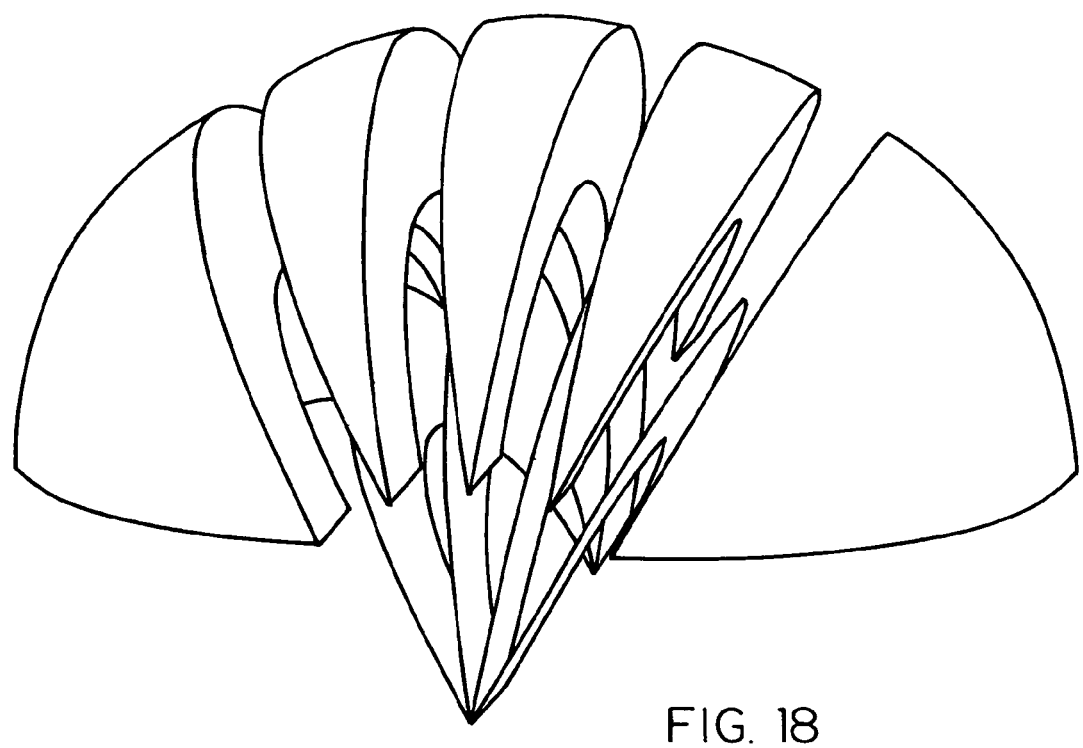
FIGS. 18–21 illustrate the fabrication concept of the flat ribs of the lobster eye structure of FIGS. 14A and 14B.
Figure 19:
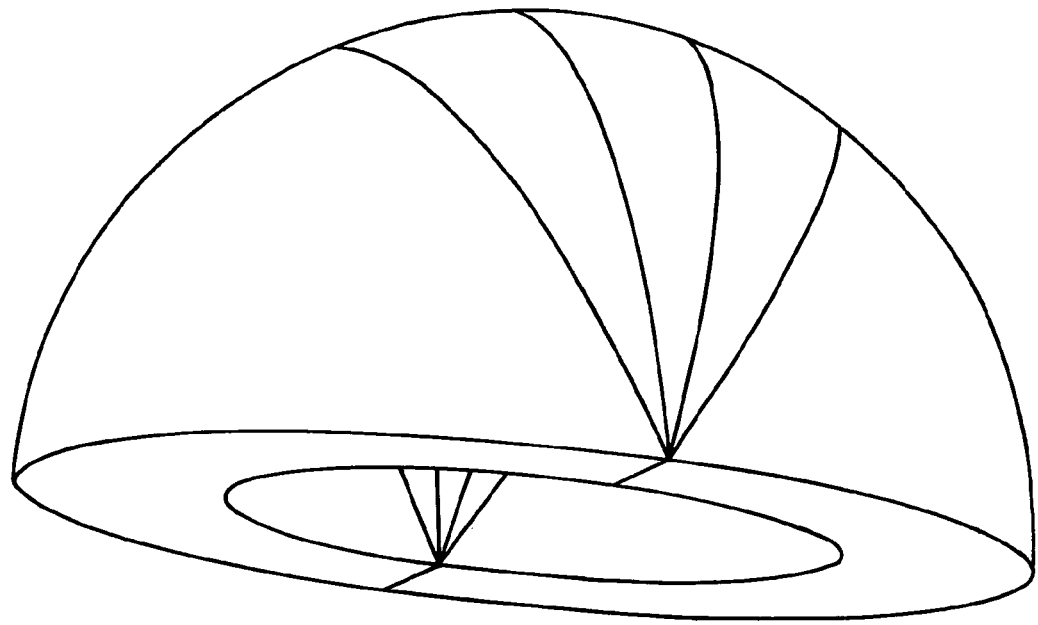

The architectural concept of this invention's Lobster Eye fabrication is depicted in FIG. 18. Thin, flat ribs are extracted from a hemispherical dome (See FIG. 19) by "knife cuts" made at pre-determined angles and spacing. In FIG. 18, we see four (4) ribs being extracted.

This hollowed-out hemispherical dome, which itself was initially extracted from a solid sphere, forms the basis of this invention's fabrication architecture. The cutting planes, which "slice" this partially hollowed out sphere, are laid out at predetermined angles and spacing, radiating from a line segment defined by points A and A', around the inner circumference and points B and B', around the outer circumference of the circular portion of this "dome", which bisect said dome. The result is a plurality of flat ribs each of which is a segment of an annulus.

Figure 20:
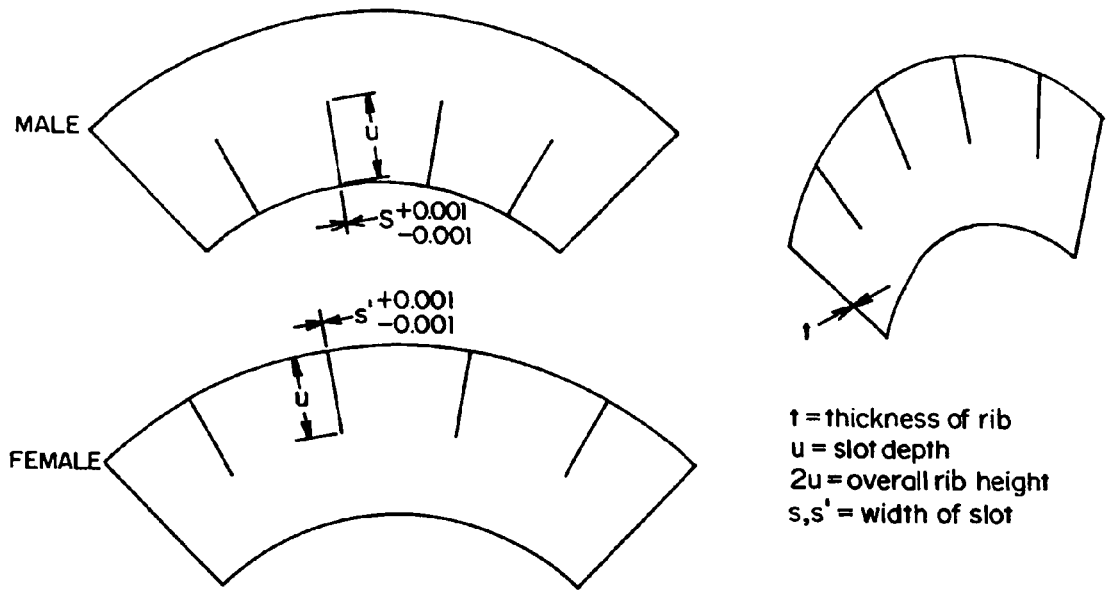

The geometry of the male and female ribs as shown in FIG. 20 are such that the depth of their mating slots is of length u on the male rib, and u' on the female rib, where u equals u' (u=u'). The height of the male rib is 2u, and the height of the female rib is 2u', such that when arranged decussately and interleaved, the male and female ribs will "snug fit" together in such a fashion that the upper curved edges of the male and female ribs are flush, and the lower curved edges of the male and female ribs are also flush. Once assembled in this fashion, the original "hemispherical dome" is recreated, "skeleton-like"—without the "unwanted" solid sections that were originally "filling" the trapezoidal cavities. This precision assembly is made possible due to the fact that the slots on the male rib are of width s, and the slots on the female rib are of width s', such that width s equals s' (s=s') and both the male and female ribs are of thickness t, such that widths s and s' equals width t (s=s'=t). However, the manufacturing tolerances are such that in physical realization, the actual width of the slots in the ribs are of width s, +0.001"/−0.000", while the actual thickness of the ribs are of width t', +0.000"/−0.001". This very slight under-sizing of the rib thickness (t), along with the very slight over-sizing of the slots (s, s') in the ribs makes it possible for the body of each male rib to just barely slip into the slots in the female ribs, and for the body of each female rib to just barely slip into the slots in the male ribs, allowing for the 90-degree (90°) crisscross interleaving of the male and female ribs.

Figure 21:
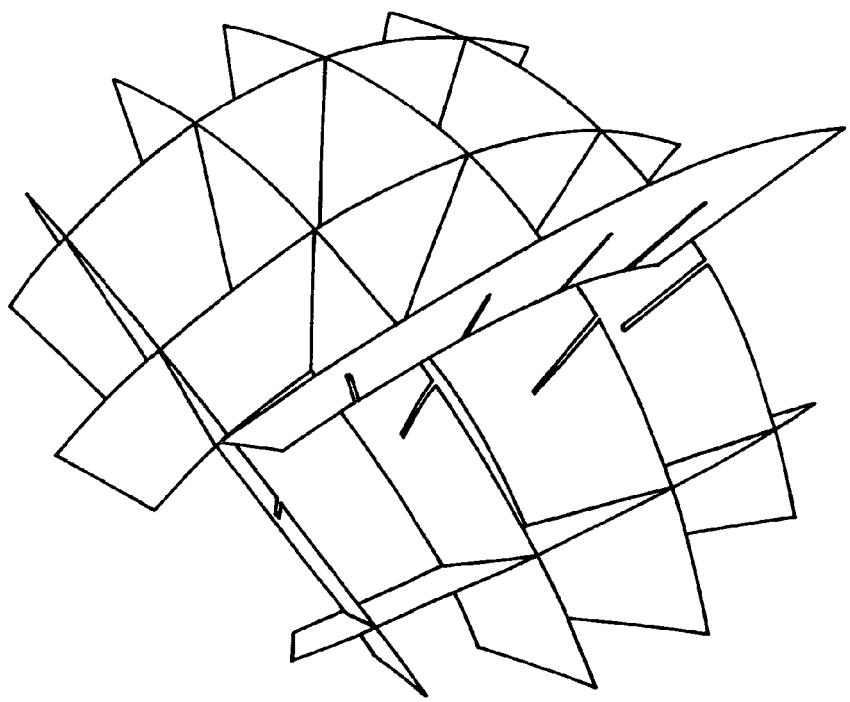

A "4×4" Lobster Eye formed by the decussate (crisscross) arrangement of four (4) pairs of the male and female wafer-like ribs of the current invention is shown in FIG. 21. One of the "male" ribs is shown in the unmated stage. Lowering this male rib vertically into the nearly complete structure below it, such that it "mates" with the four (4) "female" ribs that are designed to accept it will complete the formation of a "4×4" Lobster Eye.

It will now be understood that what has been disclosed herein constitutes a significant advance in the art of X-ray imaging technology. A novel use of lobster eye lens technology in a backscattering X-ray application provides profound improvement that has advantageous applications in a number of imaging scenarios such as in inspection of cargo containers, detection of buried mines and even in medical diagnostics. Moreover, a unique lobster eye fabrication concept permits relatively easy and low cost assembly of extremely efficient and precise structures particularly for X-ray imaging purposes. Moreover, a better understanding of lobster eye optics and detector physics offers an opportunity to improve the resulting image generation and to use that structure in new applications such as spectroscopy. Accordingly, the scope hereof is limited only by the appended claims and their equivalents.

We claim:

1. A backscatter-based X-ray staring imaging apparatus comprising:
    at least one X-ray generator for irradiating a selected target with a non-scanning beam;
    an X-ray focusing device positioned for receiving X-ray backscatter from said irradiated target; and
    a detector positioned relative to said focusing device for forming an image from said received X-ray backscatter;
    wherein said focusing device comprises a lobster eye structure;
    wherein said lobster eye structure comprises a decussate arrangement of interleaved wafer-thin flat ribs configured as a unitary three-dimensional meshed array forming a plurality of contiguous channels of continuously diminishing square cross-section, each of said flat ribs being a segment of an annulus having an inner circumference and an outer circumference.

2. The imaging apparatus recited in claim 1 wherein each of said flat ribs has a polished reflective surface and a plurality of spaced mating slots for being interleaved with other flat ribs.

3. The imaging apparatus recited in claim 1 wherein said detector comprises a digital device for converting said focused X-ray backscatter into an electronic image.

4. The imaging apparatus recited in claim 3 wherein said digital device comprises a scintillating screen coupled to a COD matrix by a fiber optic taper.

5. The imaging apparatus recited in claim 4 wherein said scintillating screen comprises a microchannel plate having a plurality of microchannels filled with a scintillating material.

6. An X-ray inspection system for generating an image of at least one object hidden behind a wall; the system comprising:
    at least one X-ray source generating open cone X-ray radiation for irradiating an area to be inspected which area includes said wall and object;
    a digital X-ray imaging detector for converting an X-ray image into an electronic image;
    a lobster eye-based X-ray focusing structure for receiving and focusing X-ray radiation backscattered from said inspected area and onto said imaging detector for imaging said at least one object;
    wherein said lobster eye-based X-ray focusing structure comprises a decussate arrangement of interleaved wafer-thin flat ribs configured as a unitary three-dimensional meshed array forming a plurality of contiguous channels of continuously diminishing square cross-section, each of said flat ribs being a segment of an annulus having an inner circumference and an outer circumference.

7. The X-ray inspection system recited in claim 6 wherein said X-ray source open cone radiation is a non-scanning, staring-type X-ray beam.

8. The X-ray inspection system recited in claim 6 wherein each of said flat ribs is coated with an X-ray reflective material.

9. The X-ray inspection system recited in claim 6 wherein each of said flat ribs has a plurality of spaced slots for being interleaved with other said flat ribs.

10. A lobster eye lens comprising:
    a decussate arrangement of interleaved wafer-thin flat ribs configured as a three-dimensional array forming a plurality of contiguous channels of continuously diminishing square cross-section;
    wherein each of said flat ribs is a segment of an annulus having an inner circumference and an outer circumference.

11. The lobster eye lens of claim 10 wherein said flat ribs are configured to provide said channels of selected length and cross-section for focusing incident X-rays.

12. The lobster eye lens of claim 11 wherein each of said flat ribs has a surface which is made highly reflective to said incident X-rays.

13. The lobster eye lens of claim 10 wherein each of said flat ribs has a plurality of spaced slots for being interleaved with other said flat ribs.

14. A lobster eye lens comprising:
a decussate arrangement of interleaved wafer-thin flat ribs configured as a three-dimensional array forming a plurality of contiguous channels of continuously diminishing square cross-section;
wherein each of said flat ribs is a segment of an annulus having an inner circumference and an outer circumference and wherein a first plurality of said flat ribs have slots extending from said inner circumference and a second plurality of said flat ribs have slots extending from said outer circumference.

15. The lobster eye lens of claim 14 wherein said decussate arrangement of said interleaved flat ribs is formed by precisely perpendicular mating said first plurality of flat ribs with said second plurality of flat ribs along said slots.

16. The lobster eye lens of claim 15 wherein the thickness of said flat ribs is substantially equal to the width of said slots and the length of said slots is substantially equal to one-half the distance between said inner circumference and said outer circumference along a radius of said annulus.

17. An X-ray imaging system comprising at least one-X-ray source for generating X-ray energy toward a proximate target area, a detector having a focal surface for receiving backscatter X-rays reflected from the target area, and a lobster eye lens for focusing said backscatter X-rays onto said detector focal surface;
said lobster eye lens having a decussate arrangement of interleaved wafer thin flat ribs configured as a three-dimensional array forming a plurality of contiguous channels of continuously diminishing square cross-section;
said flat ribs being a segment of an annulus having an inner circumference and an outer circumference.

18. An angular staring spectrometer comprising:
an X-ray source positioned at a first selected location relative to a sample to be analyzed;
a lobster eye lens positioned at a second selected location relative to said sample, said lens having a focusing surface; and
a plurality of X-ray detectors located on said focusing surface as an array of detectors selectively spaced from each other to provide an output based upon the cross-sectional geometry of the scattering cone generated by the X-ray backscatter from said sample which is indicative of the material of said sample;
said lobster eye lens having a decussate arrangement of interleaved wafer thin flat ribs configured as a three-dimensional array forming a plurality of contiguous channels of continuously diminishing square cross-section;
said flat ribs being a segment of an annulus having an inner circumference and an outer circumference.

19. A method of generating an image of objects in an area being inspected; the method comprising the steps of:
irradiating said area with X-ray energy;
positioning a detector for receiving X-ray backscatter from said irradiated area; and
placing an X-ray lobster eye lens between said area and said detector for focusing said X-ray backscatter onto said detector;
said lobster eye lens having a decussate arrangement of interleaved wafer thin flat ribs configured as a three-dimensional array forming a plurality of contiguous channels of continuously diminishing square cross-section;
said flat ribs being a segment of an annulus having an inner circumference and an outer circumference.

20. The method recited in claim 19 further comprising the step of configuring said detector for converting said focused X-ray backscatter into an electronic image of said area being inspected.

21. The method recited in claim 20 further comprising the step of locating said lobster eye lens relative to said area being inspected so that the image of said area will be responsive only to objects having elements with low Z-numbers to enhance the contrast of such objects in the image.

* * * * *